United States Patent
Yamaguchi et al.

(10) Patent No.: US 9,089,561 B2
(45) Date of Patent: Jul. 28, 2015

(54) METHODS FOR TREATING DEPRESSION, NEURODEGENERATION, INHIBITING AMYLOID β DEPOSITION, DELAYING SENESCENCE, AND EXTENDING LIFE SPANS WITH HETEROCYCLIC COMPOUNDS

(71) Applicant: ZENYAKU KOGYO KABUSHIKI KAISHA, Tokyo (JP)

(72) Inventors: Yoshimasa Yamaguchi, Tokyo (JP); Toshiyuki Matsuno, Tokyo (JP); Kenichi Saitoh, Tokyo (JP)

(73) Assignee: ZENYAKU KOGYO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/178,425

(22) Filed: Feb. 12, 2014

(65) Prior Publication Data

US 2014/0171452 A1 Jun. 19, 2014

Related U.S. Application Data

(62) Division of application No. 11/872,408, filed on Oct. 15, 2007, now abandoned.

(30) Foreign Application Priority Data

Oct. 13, 2006 (JP) ................................. 2006-280768

(51) Int. Cl.
| | |
|---|---|
| A61K 31/40 | (2006.01) |
| A61K 31/4015 | (2006.01) |
| A61K 31/495 | (2006.01) |
| A61K 31/425 | (2006.01) |
| A61K 31/426 | (2006.01) |
| A61K 31/437 | (2006.01) |
| A61K 31/429 | (2006.01) |
| A61K 31/438 | (2006.01) |
| A61K 31/519 | (2006.01) |
| C07D 471/04 | (2006.01) |
| C07D 471/10 | (2006.01) |
| C07D 487/04 | (2006.01) |
| C07D 487/10 | (2006.01) |
| C07D 513/04 | (2006.01) |
| C07D 513/20 | (2006.01) |
| A61K 31/444 | (2006.01) |
| A61K 31/4745 | (2006.01) |

(52) U.S. Cl.
CPC .............. *A61K 31/437* (2013.01); *A61K 31/40* (2013.01); *A61K 31/4015* (2013.01); *A61K 31/425* (2013.01); *A61K 31/426* (2013.01); *A61K 31/429* (2013.01); *A61K 31/438* (2013.01); *A61K 31/444* (2013.01); *A61K 31/4745* (2013.01); *A61K 31/495* (2013.01); *A61K 31/519* (2013.01); *C07D 471/04* (2013.01); *C07D 471/10* (2013.01); *C07D 487/04* (2013.01); *C07D 487/10* (2013.01); *C07D 513/04* (2013.01); *C07D 513/20* (2013.01)

(58) Field of Classification Search
CPC . A61K 31/40; A61K 31/4015; A61K 31/495; A61K 31/425; A61K 31/426
USPC ....................................................... 514/259.1
See application file for complete search history.

(56) References Cited

U.S. PATENT DOCUMENTS

| | | | |
|---|---|---|---|
| 4,337,260 | A | 6/1982 | Tashiro et al. |
| 5,100,645 | A | 3/1992 | Ali-Khan et al. |
| 5,464,843 | A | 11/1995 | Hansen, Jr. et al. |
| 5,965,568 | A | 10/1999 | Kakihana et al. |
| 6,635,652 | B1 | 10/2003 | Kawashima et al. |
| 7,141,579 | B2 | 11/2006 | Kawashima et al. |
| 7,244,739 | B2 | 7/2007 | Cheng et al. |
| 2003/0147882 | A1 | 8/2003 | Solomon et al. |
| 2004/0087614 | A1 | 5/2004 | Baumann et al. |
| 2005/0272735 | A1 | 12/2005 | Xie et al. |

FOREIGN PATENT DOCUMENTS

| | | |
|---|---|---|
| EP | 1 219 621 A1 | 7/2002 |
| EP | 1 357 124 A1 | 10/2003 |
| FR | 2 874 611 | 3/2006 |
| JP | 2005-314348 | 11/2005 |

(Continued)

OTHER PUBLICATIONS

Yoshimasa Yamaguchi, et al. "Enhancement of Acetylcholine Release by Cognitive Enhancers ZSET845 and ZSET1446 in the Rat Hippocampus" The 25th Annual Meeting of Japan Neuroscience Society, Jul. 2002.

S. Kawashima, et al. "Stimulation of Acetylcholine Release in Rat Hippocampus by Cognitive Enhancers ZSET845 and ZSET1446" The 8th International Conference on Alzheimer's Disease and Related Disorders Stockholm, Sweden, (5 pp.) Jul. 2002, w/ Abstract.

K. Saitoh, et al. "Synthesis. Biological Evaluation and Structure-Activity Relationship of 3,3-Disubstituted Azaindolizinone Derivatives as Potent Nootropic Agents" (4pp.) Nov. 2002, w/ English Abstract.

S. Kawashima, et al. "Stimulation of Acetylcholine Release in the Rat Hippocampus and Cerebral Cortex by 3,3-Disubstituted Azaindolizinone Derivatives" Federation of American Societies for Experimental Biology; vol. 17, No. 4, (2pp.) Mar. 2003.

(Continued)

*Primary Examiner* — Yong Chong
(74) *Attorney, Agent, or Firm* — Oblon, McClelland, Maier & Neustadt, L.L.P.

(57) ABSTRACT

Disclosed is an antidepressant, neuroprotectant, amyloid β deposition inhibitor, or age retardant composition containing a heterocyclic compound having the general formula (I):

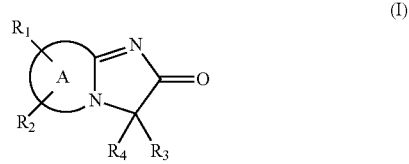

2 Claims, 4 Drawing Sheets

(56) References Cited

FOREIGN PATENT DOCUMENTS

| WO | WO 03/035649 A1 | 5/2003 |
|---|---|---|
| WO | 2005/079780 | 9/2005 |
| WO | WO 2006/049890 A1 | 5/2006 |
| WO | WO 2008/047951 A2 | 4/2008 |
| WO | WO 2008/047952 A2 | 4/2008 |

OTHER PUBLICATIONS

Y. Yamaguchi, et al. "Effects of Azaindolizinone Derivatives ZSET845 and ZSET 1446 on Acetylcholine Release in the Cortex and Learning Impairments in the Rat" 6$^{th}$ International conference AD/PD 2003 (2pp.) May 2003.
S. Kawashima et al. "Stimulation of Acetylcholine and Dopamine Release in the Rat Hippocampus by Azaindotizinone Derivatives and Recovery of Learning Impairment in the Rat" Experimental Biology; Apr. 2004 (1pp.).
Y. Yamaguchi, et al. "Effects of a Novel Cognitive Enhancer ZSET1446 on Impairments of Learning induced by amyloid β 1-40 in Rats" 7$^{th}$ International Conference AD/PD (1pp); Mar. 2005.
Yoshimasa Yamaguchi, et al. "Effects of a Novel Cognitive Enhancer, Spiro[imidazo-[1,2-a] pyridine-3,2-indan] -2(3H)-one (ZSET1446), on Learning Impairments Induced by Amyloid-β 1-40 in the Rat" The Journal of Pharmacology and Experimental Therapeutics, vol. 317; No. 3, (1079-1087), 2006.
Yukio Ito, et al. "A Novel Azaindolizinone Derivative ZSET1446 (Spiro[imidazo[1,2-a] pyridine-3,2-indan] -2(3H)-one) Improves Methamphetamine-Induced Impairment of Recognition Memory in Mice by Activating Extracellular Signal—Regulated Kinase 1/2" The Journal of Pharmacology and Experimental Therapeutics, vol. 320 No. 2 (819-827), 2006.
Y. Yamaguchi, et al. Neuro-degenerative Diseases; 8th International Conference AD/PD; (3pp) Mar. 2007.
Norifumi Shioda, et al. "Novel Cognitive Enhancer, ZSET1446 Promotes Neurogenesis in the Hippocampal dentate Gyrus and Improves Depressive Behavior in the Olfactory bulbectomized Mice"; Biofunction and Drug Discovery Symposium; Sep. 2007 w/ English Abstract.
Norifumi Shioda, et al. "Effects of a Novel Cognitive Enhancer ZSET1446 on depressive behavior and neurogenesis in the dentate gyrus of olfactory bulbectomized mice" 37th Annual Meeting of the Society for Neuroscience (15pp); Nov. 2007.
Hiroshi Kurihara, et al. "Inhibitory Effect of Oolong Tea on the Oxidative State of Low Density Lipoprotein (LDL)" Biol. Pharm. Bull. 26 (5) (739-742) 2003.
Joseph Knoll, et al. "The Striatal Dopamine Dependency of Life Span in Male Rats. Longevity Study with (−) Deprenyl" Mechanisms of Ageing and Development, 46; (237-262) 1998.
The Japan Stroke Society:Clinical Guidline for Stroke (2004), (42-43).
Pharmacia, Japanese Pharmacology Association, vol. 38, No. 9, (891-892) 2002.
"Acute Brain Infarction" Stroke Treatment Guidelines (2004), (42-43).
Chihiro Tohda, et al. "Curcumin, an Ingredient in Curry Spice, Prevents Alzheimer's Disease" Japanese Pharmacology Association, vol. 38, No. 9, (891-892) 2002.
Y. Yamaguchi, et al., "Effects of ZSET845 and ZSET1446 on Acetylcholine Release in the Cortex and Learning Impairments in the Rat" Database CA [Online] Chemical Abstracts Service. Database accession No. 2005:332348, XP002504721, 2 pages.
Yoshimasa Yamaguchi. et al., "Antiamnesic Effects of Azaindolizinone Derivative ZSET845 on Impaired Learning and Decreased ChAT Activity Induced by Amyloid-β 25-35 in the Rat", Brain Research, vol. 945, No. 2, XP002504719, Jan. 1, 2002, pp. 259-265.
Yoshimasa Yamaguchi, et al., "Ameliorative Effects of Azaindolizinone Derivative ZSET845 on Scopolamine-Induced Deficits in Passive Avoidance and Radial-Arm Maze Learning in the Rat", Japanese Journal of Pharmacology, vol. 87, No. 3, XP001098397, Nov. 1, 2001,pp. 240-244.
Michael S. Rafii et al., "Recent developments in Alzheimer's disease therapeutics", Bio-Med Central, BMC Medicine 2009, 7:7, pp. 1-4.
Hans Basun, et al., Plasma Levels of Aβ42 and Aβ40 in Alzheimer Patients during Treatment with the Acetylcholinesterase Inhibitor Tacrine, Dement Geriatr Cogn Disord 2002; 14, pp. 156-160.
Hongxin Dong, et al., "Acetylcholinesterase inhibitors ameliorate behavioral deficits in the Tg2576 mouse model of Alzheimer's disease", National Institute of Health, Psychopharmacology (Berl), Aug. 2005; 181(1), pp. 145-152.
Office Action issued Aug. 27, 2010, in China Patent Application No. 200780038180.0 (with English translation).
Eurasian Office Action dated Sep. 9, 2010 in corresponding Eurasian Application No. 200970372 filed on Oct. 15, 2007 (with English Translation).
Eurasian Office Action dated Sep. 9, 2010 in corresponding Eurasian Application No. 200970373 filed on Oct. 15, 2007 (with English Translation).
New Zealand Office Action dated Jul. 16, 2010 in corresponding New Zealand Application No. 576163.
New Zealand Office Action dated Jul. 16, 2010 in corresponding New Zealand Application No. 576164.
Chinese Office Action issued Jan. 18, 2011, in Patent Application No. 200780038180.0 (with English-language translation).
Chinese Office Action issued Jan. 5, 2011, in Patent Application No. 200780038210.8 (with English-language translation).
Office Action issued Feb. 1, 2011 in Canada Application No. 2,666,360.
Office Action issued Feb. 2, 2011 in Canada Application No. 2,666,258.
Office Action issued Feb. 10, 2011 in Singapore Application No. 200902429-0.
European Search Report dated Dec. 23, 2011 as received in the corresponding European Patent Application No. 11006539.8-1216/ 2388002.
Kazufumi Akiyama, "Longitudinal Clinical Course Following Pharmacological Treatment of Methamphetamine Psychosis which Persists after Long-Term Abstinence", Ann. N.Y. Acad. Sci. 1074: 125-134 (2006).
European Search Report dated Dec. 6, 2011 as received in the corresponding European Patent Application No. 11006537.2-1216/ 2388000.
Mahesh, R., et al., "Microwave-Assisted Solvent-Free Synthesis of 3-[(4-substituted piperazin-1-yl)alkyl] imidazo[2,1-b][1,3]benzothiazol-2(3H)-ones as serotonin$_3$) receptor antagonists", Pharmazie, vol. 60, No. 6, Jun. 2005, pp. 411-414.
Yoshifumi Kagami-Shi, et al., "Neuroprotective effect of 5-HT$_3$ receptor antagonist on ischemia-induced decrease in CA1 field potential in rat hippocampal slices" European Journal of Pharmacology, 224 (1992), pp. 51-56.
Hyun Joo Lee, et al., "Blockade of 5-HT$_3$ receptor with MDL7222 and Y25130 reduces hydrogen peroxide-induced neurotoxicity in cultured rat cortical cells", Life Sciences, 78 (2005), pp. 294-300.
Ju Yeon Ban, et al., "Blockade of 5-HT$_3$ receptor with MDL72222 and Y25130 reduces β-amyloid protein (25-35)-induced neurotoxicity in cultured rat cortical neurons", European Journal of Pharmacology, 520 (2005), pp. 12-21.
European Search Report dated Dec. 13, 2011 as received in the corresponding European Patent Application No. 11006538.0-1216/ 2388001.
Combined Taiwanese Office Action and Search Report Issued Aug. 27, 2012, in Taiwanese Patent Application No. 096138439 with English translation.
Office Action issued Sep. 4, 2012 in European Patent Application No. 07 830 697.4.
Jorge Ghiso, et al., "Amyloidosis and Alzheimer's disease" Advanced Drug Delivery Reviews, vol. 54, No. 12, XP55036559A, Dec. 1, 2002, pp. 1539-1551.

METHODS FOR TREATING DEPRESSION, NEURODEGENERATION, INHIBITING AMYLOID β DEPOSITION, DELAYING SENESCENCE, AND EXTENDING LIFE SPANS WITH HETEROCYCLIC COMPOUNDS

CROSS REFERENCE TO RELATED APPLICATIONS

This application is a divisional of U.S. application Ser. No. 11/872,408 filed Oct. 15, 2007, abandoned, and incorporated herein by reference, and claims benefit to JP 2006-280768 filed Oct. 13, 2006.

FIELD OF THE INVENTION

The present invention is in the filed of medicinal chemistry and relates to an antidepressant, neuroprotectant, amyloid β deposition inhibitor, or age retardant composition comprising containing a heterocyclic compound having a specific structure.

BACKGROUND OF THE INVENTION

Among drugs currently used in drug therapy for depression and panic disorder, fluvoxamine maleate (1991) and paroxetine hydrochloride (2000) were developed as selective serotonin reuptake inhibitors (SSRI). SSRI is a first-line drug for both acute treatment and long-term treatment of depression and panic disorder. However, SSRI has some issues such as drug effects appearing only through chronic administration, drug withdrawal because of adverse effects, and side effects including withdrawal signs and influence on cognitive functions. Therefore, there is a strong demand for development of effective drugs having an immediate activity and fewer side effects.

One of factors involved with ageing is oxidative stress. Antioxidative substances reportedly have antiaging activity. For example, oolong tea containing antioxidants is considered to have antiaging activity (*Biol Pharm Bull* Vol 26 No 5 739-742 2003). On the other hand, while deprenyl reportedly increases the survival rate and is used as a monoamine oxidase B inhibitor in treatment for Parkinson's disease, this has been confirmed to be due to its antioxidant activity (*Mech Ageing Dev* Vol 46 No 1-3 237-262 1988). However, these substances do not offer antiaging activity and increase in the survival rate of animals at satisfactory levels.

Edaravone is a free radical scavenger having antioxidative activity and used as a neuroprotectant. However, it is not highly effective and various side effects including kidney failure have been reported (The Japan Stroke Society:Clinical Guidline for Stroke (2004), 42-43).

Curcumin is a component of *Curcuma longa* contained in curry in a large amount and has antiinflammatory and antioxidative activity equivalent to prescribed nonsteroidal antiinflammatory drugs (NSAIDs). Studies have shown that curcumin inhibits amyloid-related pathologies (*Pharmacia*, Japanese Pharmacology Association, Vol. 38, No. 9, 891-892, 2002). However, curcumin does not inhibit amyloid deposition at satisfactory levels.

Booklet of International Publication No. 01/009131 and Booklet of International Publication No. 2002/060907 disclose brain function improvers containing heterocyclic compounds having specific structures. The heterocyclic compounds are disclosed as brain function improvers leading to treatment for memory loss and memory acquisition/retention disorder in senile dementia, Alzheimer's disease and related disorders. Other effects useful as antidepressant, neuroprotectant, amyloid β inhibitor, and age retardant are not disclosed.

SUMMARY OF THE INVENTION

The present invention provides an antidepressant, neuroprotectant, amyloid β deposition inhibitor, or age retardant containing a heterocyclic compound having the general Formula (I):

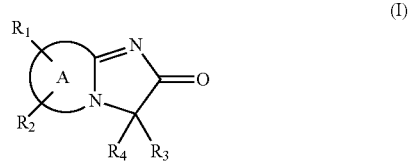

or a pharmaceutically acceptable salt or hydrate thereof.

In the general Formula (I), the structural unit having the general formula (II) is one or more structural units selected from multiple types of structural units having the general Formula (M).

(II)

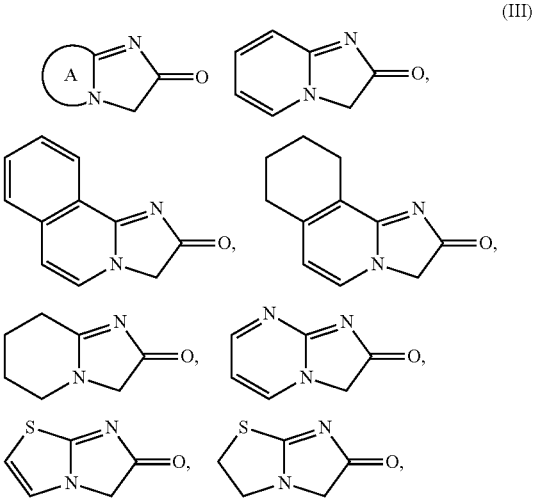

In the general Formula (I), $R_1$ and $R_2$ each are one or more functional groups independently selected from the group consisting of a hydrogen atom, halogen atom, hydroxy group, amino group, acetylamino group, benzylamino group, trifluoromethyl group, $C_1$-$C_6$ alkyl group, $C_1$-$C_6$ alkoxy group, and —O—$(CH_2)$n-$R_5$, wherein $R_5$ is a vinyl group, $C_3$-$C_6$ cycloalkyl group, or phenyl group, and n is 0 or 1.

Furthermore, in the general Formula (I), $R_3$ and $R_4$ each are one or more functional groups independently selected from the group consisting of a hydrogen atom, $C_1$-$C_6$ alkyl group, $C_3$-$C_8$ cycloalkyl group, and —CH($R_7$)—$R_6$; alternatively, $R_3$ and $R_4$ together form a spiro ring having the general Formula (IV):

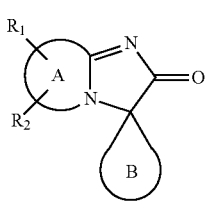

(IV)

$R_6$ is one or more functional groups selected from the group consisting of a vinyl group; ethinyl group; phenyl optionally substituted by a $C_1$-$C_6$ alkyl group, $C_1$-$C_6$ alkoxy group, hydroxy group, 1 or 2 halogen atoms, di $C_1$-$C_6$ alkylamino group, cyano group, nitro group, carboxy group, or phenyl group; phenethyl group; pyridyl group; thienyl group; and furyl group. The above $R_7$ is a hydrogen atom or $C_1$-$C_6$ alkyl group.

Furthermore, in the general Formula (IV), the structural unit B is one or more structural units selected from multiple types of structural units having the general Formula (V). The structural unit B binds at a position marked by * in the general Formula (V) to form a spiro ring.

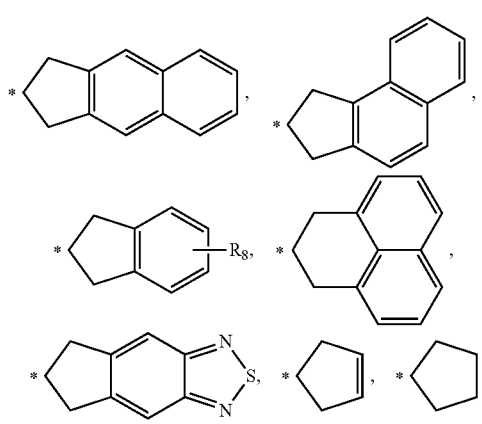

(V)

$R_8$ is one or more functional groups selected from the group consisting of a hydrogen atom, halogen atom, hydroxy group, $C_1$-$C_6$ alkoxy group, cyano group, and trifluoromethyl group.

The compounds of Formula (I) may be used as an antidepressant, neuroprotectant, amyloid β deposition inhibitor, delayer of senescence, as an age retardant and extender of life spans of animals.

The invention relates in particular to a method of treating or preventing depression, manic depressive psychoses, obsessive-compulsive disorder, panic disorder, or anxiety disorder in a mammal in need thereof, comprising administering to the mammal an effective amount of a heterocyclic compound having the general Formula (I), or a pharmaceutically acceptable salt or hydrate thereof.

The invention also relates to a method of reducing or preventing neurodegeneration in a mammal in need thereof, comprising administering to the mammal an effective amount of a compound having the general Formula (I), or a pharmaceutically acceptable salt thereof. In one embodiment, the neurodegeneration is the result of one or more cerebrovascular disorders selected from the group consisting of transient ischemic attack, cerebral hemorrhage, subarachnoid hemorrhage, intracranial hemorrhage, cerebral infarct, and/or hypertensive encephalopathy.

The invention also relates to a method of inhibiting amyloid deposition in an mammal in need thereof, comprising administering to the mammal an effective amount of a compound having the general Formula (I). In one embodiment, the amyloid deposition is the result of or associated with one or more amyloid-related pathologies selected from amyloidosis, cerebral amyloid angiopathy, cataract, glaucoma, the progression of glaucoma, age-related macular degeneration, rheumatism, osteoporosis, metabolic syndrome, wrinkles, and hair loss.

The invention also relates to a method of delaying senescence is an animal in need thereof, comprising administering to the animal an effective amount of a heterocyclic compound having the general Formula (I). In one embodiment, the invention provides an improvement and/or delay in worsening symptoms of one or more conditions associated with senescence, including reactivity, passivity, glossiness and/or coarseness of hair, hair loss, ulcers, periophthalmic lesions, cataracts, corneal opacity and/or lordokyphosis.

The invention also relates to a method of extending the life span of a mammal in need thereof, comprising administering to the mammal an effective amount of a compound having the general Formula (I).

BEST MODES FOR CARRYING OUT THE INVENTION

Figure 1:
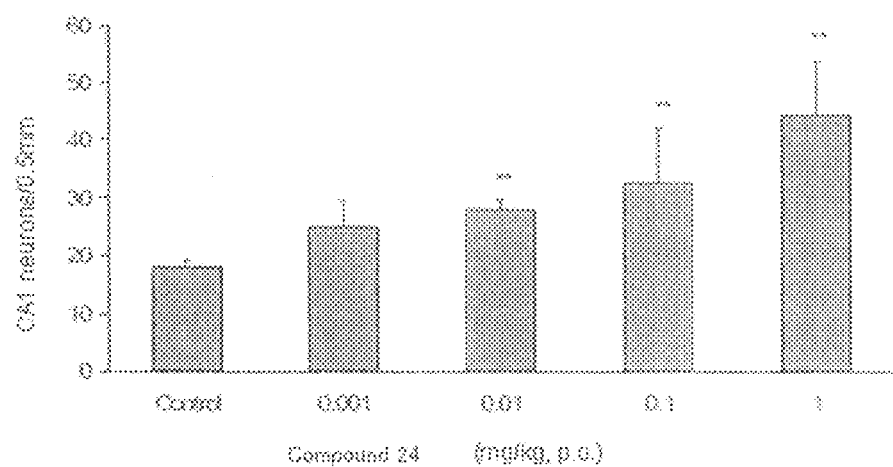
FIG. 1 is a graphical representation for explaining the hippocampus CA1 region protective activity of Compound 24 in the gerbil transient forebrain ischemia model.

Embodiments of the present invention are described hereafter. Embodiments below relate to an antidepressant, neuroprotectant, amyloid β deposition inhibitor, or age retardant composition containing a heterocyclic compound having the above described specific structure (azaindolizinone derivatives) and pharmaceutically acceptable carriers or diluents.

The compounds useful in the present invention all contain a heterocyclic compound having the general Formula (I):

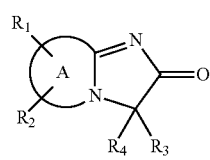

(I)

or a pharmaceutically acceptable salt or hydrate thereof.

In the general Formula (I), the structural unit having the general Formula (II) is one or more structural units selected from multiple types of structural units having the general Formula (III).

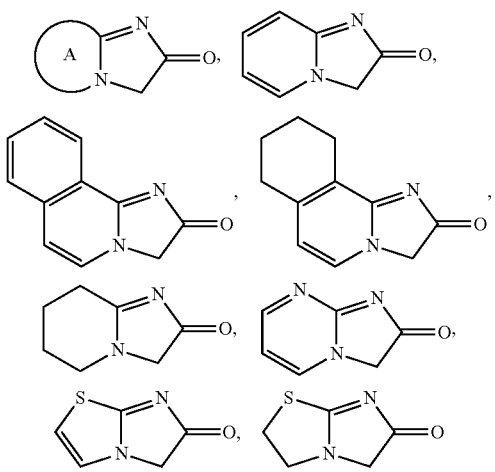

(III)

Furthermore, in the general formula (I), $R_1$ and $R_2$ each are one or more functional groups independently selected from the group consisting of a hydrogen atom, halogen atom, hydroxy group, amino group, acetylamino group, benzylamino group, trifluoromethyl group, $C_1$-$C_6$ alkyl group, $C_1$-$C_6$ alkoxy group, and —O—$(CH_2)n$-$R_5$, wherein $R_5$ is a vinyl group, $C_3$-$C_6$ cycloalkyl group, or phenyl group, and n is 0 or 1.

Furthermore, in the general Formula (I), $R_3$ and $R_4$ each are one or more functional groups independently selected from the group consisting of a hydrogen atom, $C_1$-$C_6$ alkyl group, $C_3$-$C_8$ cycloalkyl group, and —CH($R_7$)—$R_6$; alternatively, $R_3$ and $R_4$ together form a spiro ring having the general formula (IV):

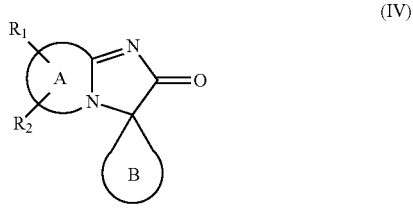

(IV)

The above $R_6$ is one or more functional groups selected from the group consisting of a vinyl group; ethinyl group; phenyl optionally substituted by a $C_1$-$C_6$ alkyl group, $C_1$-$C_6$alkoxy group, hydroxy group, 1 or 2 halogen atoms, di $C_1$-$C_6$ alkylamino group, cyano group, nitro group, carboxy group, or phenyl group), phenethyl group, pyridyl group, thienyl group, and furyl group. The above $R_7$ is a hydrogen atom or $C_1$-$C_6$ alkyl group.

In the general Formula (IV), the structural unit B is one or more structural units selected from multiple types of structural units having the general Formula (V). The structural unit B binds at a position marked by * in the general Formula (V) to form a spiro ring.

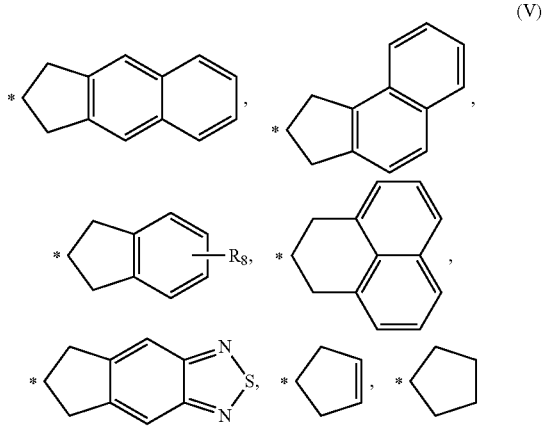

(V)

Here, $R_8$ is one or more functional groups selected from the group consisting of a hydrogen atom, halogen atom, hydroxy group, $C_1$-$C_6$alkoxy group, cyano group, and trifluoromethyl group.

When the heterocyclic compound having the general Formula (I) has asymmetric carbon atoms in the structure, its isomer from asymmetric carbon atoms and their mixture (racemic modification) is present. In such cases, all of them are included in the heterocyclic compound used in the embodiments described later.

The heterocyclic compound has the general Formula (I). In the general Formula (I), the following terms have the meanings specified below along with their examples.

The term "$C_1$-$C_6$" refers to 1 to 6 carbon atoms unless otherwise defined. The term "$C_3$-$C_8$" refers to 3 to 8 carbon atoms unless otherwise defined. The term "$C_1$-$C_6$ alkyl" includes linear or branched alkyl groups such as methyl, ethyl, n-propyl, isopropyl, n-butyl, tert-butyl, sec-butyl, n-pentyl, and n-hexyl. The term "$C_1$-$C_6$ alkoxy" includes linear or branched alkoxy groups such as methoxy, ethoxy, n-propoxy, isopropoxy, n-butoxy, tert-butoxy, sec-butoxy, n-pentyloxy, and n-hexyloxy. The term "$C_3$-$C_8$ cycloalkyl" includes cyclopropyl, cyclobutyl, cyclopentyl, cyclohexyl, cycloheptyl, and cyclooctyl. The term "halogen atom" includes fluorine, chlorine, bromine, and iodine.

The heterocyclic compound useful in the practice of the present invention is not particularly restricted as long as it has the above described specific structure. For example, the following compounds can be used.

3,3-dimethylimidazo[1,2-a]pyridin-2(3H)-one, 3,3-dipropylimidazo[1,2-a]pyridin-2(3H)-one,
3,3-dibutylimidazo[1,2-a]pyridin-2(3H)-one, 3,3-diallylimidazo[1,2-a]pyridin-2(3H)-one,
3,3-diallyl-8-benzyloxyimidazo[1,2-a]pyridin-2(3H)-one,
3,3-di(2-propinyl)imidazo[1,2-a]pyridin-2(3H)-one,
3,3-dibenzylimidazo[1,2-a]pyridin-2(3H)-one,
3,3-dibenzyl-8-methylimidazo[1,2-a]pyridin-2(3H)-one,
3,3-dibenzyl-5,7-dimethylimidazo[1,2-a]pyridin-2(3H)-one,
3,3-dibenzyl-8-hydroxyimidazo[1,2-a]pyridin-2(3H)-one,
3,3-dibenzyl-8-methoxyimidazo[1,2-a]pyridin-2(3H)-one,
3,3-dibenzyl-8-ethoxyimidazo[1,2-a]pyridin-2(3H)-one,
8-allyloxy-3,3-dibenzylimidazo[1,2-a]pyridin-2(3H)-one,
3,3-dibenzyl-8-isopropoxyimidazo[1,2-a]pyridin-2(3H)-one,
3,3-dibenzyl-8-cyclopropylmethyloxyimidazo[1,2-a]pyridin-2(3H)-one, 3,3-dibenzyl-8-cycloheptyloxyimidazo[1,2-a]pyridin-2(3H)-one,
3,3-dibenzyl-6-chloroimidazo[1,2-a]pyridin-2(3H)-one,
3,3-dibenzyl-6,8-dichloroimidazo[1,2-a]pyridin-2(3H)-one,
3,3-dibenzyl-8-chloro-6-trifluoromethylimidazo[1,2-a]pyridin-2(3H)-one,
3,3-dibenzyl-8-benzyloxyimidazo[1,2-a]pyridin-2(3H)-one,
8-amino-3,3-dibenzylimidazo[1,2-a]pyridin-2(3H)-one,
8-acetylamino-3,3-dibenzylimidazo[1,2-a]pyridin-2(3H)-one,
3,3-dibenzyl-8-benzylaminoimidazo[1,2-a]pyridin-2(3H)-one,
3,3-bis(3-chlorobenzyl)imidazo[1,2-a]pyridin-2(3H)-one,
3,3-bis(3-fluorobenzyl)imidazo[1,2-a]pyridin-2(3H)-one,
3,3-bis(4-fluorobenzyl)imidazo[1,2-a]pyridin-2(3H)-one,
3,3-bis(2,4-dichlorobenzyl)imidazo[1,2-a]pyridin-2(3H)-one,
3,3-bis(4-dimethylaminobenzyl)imidazo[1,2-a]pyridin-2(3H)-one,
3,3-bis(4-methoxybenzyl)imidazo[1,2-a]pyridin-2(3H)-one,
3,3-bis(4-biphenylmethyl)imidazo[1,2-a]pyridin-2(3H)-one,
3,3-bis(4-cyanobenzyl)imidazo[1,2-a]pyridin-2(3H)-one,
3,3-bis(4-hydroxy-benzyl)imidazo[1,2-a]pyridin-2(3H)-one,
3,3-bis(3-phenyl-1-propyl)imidazo[1,2-a]pyridin-2(3H)-one,
3,3-bis(2,4-difluorobenzyl)imidazo[1,2-a]pyridin-2(3H)-one,
3,3-bis(4-nitrobenzyl)imidazo[1,2-a]pyridin-2(3H)-one,
3,3-bis(4-carboxybenzyl)imidazo[1,2-a]pyridin-2(3H)-one,
8-benzyloxy-3,3-bis(1-phenylethyl)imidazo[1,2-a]pyridin-2(3H)-one,
8-benzyloxy-3,3-bis(3-methylbenzyl)imidazo[1,2-a]pyridin-2(3H)-one,
8-benzyloxy-3,3-bis(4-methylbenzyl)imidazo[1,2-a]pyridin-2(3H)-one,
3-benzyl-3-(4-fluorobenzyl)imidazo[1,2-a]pyridin-2(3H)-one,
3-ethyl-3(4-fluorobenzyl)imidazo[1,2-a]pyridin-2(3H)-one,
8-methyl-3,3-bis(3-pyridylmethyl)imidazo[1,2-a]pyridin-2(3H)-one,
8-methyl-3,3-bis(4-pyridylmethyl)imidazo[1,2-a]pyridin-2(3H)-one,
3,3-bis(2-thienylmethyl)imidazo[1,2-a]pyridin-2(3H)-one,
3,3-bis(2-furilmethyl)imidazo[1,2-a]pyridin-2(3H)-one,
spiro[imidazo[1,2-a]pyridin-2(3H)-one-3,2'-indan],
spiro[imidazo[1,2-a]pyridin-2(3H)-one-3,2'-[2,3]dihydrophenarene],
spiro[imidazo[2,1-b]thiazol-6(5H)-one-5,2'-benzo[f]indan],
spiro[imidazo[1,2-b]thiazol-6(5H)-one-5,2'-indan],
spiro[2-methylimidazo[1,2-b]thiazol-6(5H)-one-5,2'-benzo[f]indan],
5,5-bis(4-fluorobenzyl)imidazo[2,1-b]thiazol-6(5H)-one,
5,5-dibenzylimidazo[2,1-b]thiazol-6(5H)-one,
5,5-bis(4-methylbenzyl)imidazo[2,1-b]thiazol-6(5H)-one,
5,5-bis(4-cyanobenzyl)imidazo[2,1-b]thiazol-6(5H)-one,
5,5-dibenzyl-2-methylimidazo[2,1-b]thiazol-6(5H)-one,
5,5-bis(4-fluorobenzyl)-2-methylimidazo[2,1-b]thiazol-6(5H)-one,
5,5-dicyclohexyl-2-methylimidazo[2,1-b]thiazol-6(5H)-one,
5,5-bis(4-cyanobenzyl)-2-methylimidazo[2,1-b]thiazol-6(5H)-one,
5,5-di(2-butenyl)imidazo[2,1-b]thiazol-6(5H)-one, 5,5-dibutylimidazo[2,1-b]thiazol-6(5H)-one,
5,5-dicyclohexylimidazo[2,1-b]thiazol-6(5H)-one,
5,5-bis(2-thienylmethyl)imidazo[2,1-b]thiazol-6(5H)-one,
spiro[2,3-dihydroimidazo[2,1-b]thiazol-6(5H)-one-5,2'-benzo[f]indan],
5,5-dibutyl-2,3-dihydroimidazo[2,1-b]thiazol-6(5H)-one,
5,5-di(2-butenyl)-2,3-dihydroimidazo[2,1-b]thiazol-6(5H)-one,
5,5-bis(4-methylbenzyl)-2,3-dihydroimidazo[2,1-b]thiazol-6(5H)-one,
5,5-bis(2-thienylmethyl)-2,3-dihydroimidazo[2,1-b]thiazol-6(5H)-one,
5,5-bis(4-fluorobenzyl)-2,3-dihydroimidazo[2,1-b]thiazol-6(5H)-one,
5,5-dibenzyl-2,3-dihydroimidazo[2,1-b]thiazol-6(5H)-one,
spiro[imidazo[1,2-a]pyridin-2(3H)-one-3,2'-benzo[f]indan],
2-hydroxy-3-(2-naphthylmethyl)-imidazo[1,2-a]pyridine,
3-benzylimidazo[1,2-a]pyridin-2(3H)-one, spiro[5,6,7,8-tetrahydroimidazo[1,2-a]pyridin-2(3H)-one-3,2'-benzo[f]indan],
3,3-dicyclohexyl-5,6,7,8-tetrahydroimidazo[1,2-a]pyridin-2(3H)-one,
3,3-bis(2-thienylmethyl)-5,6,7,8-tetrahydroimidazo[1,2-a]pyridin-2(3H)-one,
3,3-dibutyl-5,6,7,8-tetrahydroimidazo[1,2-a]pyridin-2(3H)-one,
3,3-dipropyl-5,6,7,8-tetrahydroimidazo[1,2-a]pyridin-2(3H)-one,
spiro[imidazo[1,2-a]pyrimidin-2(3H)-one-3,2'-benzo[f]indan],
3,3-di(2-butenyl)imidazo[1,2-a]pyrimidin-2(3H)-one,
3,3-bis(2-thienylmethyl)imidazo[1,2-a]pyrimidin-2(3H)-one,
3,3-bis(4-fluorobenzyl)imidazo[1,2-a]pyrimidin-2(3H)-one,
3,3-dicyclohexylimidazo[1,2-a]pyrimidin-2(3H)-one,
3,3-bis(4-cyanobenzyl)imidazo[1,2-a]pyrimidin-2(3H)-one,
3,3-bis(4-methylbenzyl)imidazo[1,2-a]pyrimidin-2(3H)-one,
4,4-dibenzyl-1-methyl-5-oxo-4,5-dihydroimidazole, spiro[imidazo[1,2-a]pyridin-2(3H)-one-3,2'-(4'-fluoroindan)],
spiro[imidazo[1,2-a]pyridin-2(3H)-one-3,2'-(5'-methoxyindan)],
spiro[imidazo[1,2-a]pyridin-2(3H)-one-3,2'-(5'-iodoindan)],
spiro[imidazo[1,2-a]pyridin-2(3H)-one-3,2'-(4'-cyanoindan)],
spiro[imidazo[2,1-a]isoquinolin-2(3H)-one-3,2'-indan],
spiro[imidazo[1,2-a]pyridin-2(3H)-one-3,2'-((1,2,5-thiadiazo)[4,5-c]indan)],
spiro[imidazo[2,1-a]isoquinolin-2(3H)-one-3,2'-((1,2,5-thiadiazo)[4,5-c]indan)],
spiro[imidazo[1,2-a]pyrimidin-2(3H)-one-3,4'-(1'-cyclopentene)],
spiro[imidazo[1,2-a]pyrimidin-2(3H)-one-3,2'-indan],
spiro[imidazo[1,2-a]pyrimidin-2(3H)-one-3,2'-((1,2,5-thiadiazo)[4,5-c]indan)],
spiro[imidazo[1,2-a]pyridin-2(3H)-one-3,2'-(5'-trifluoromethylindan)],
spiro[imidazo[1,2-a]pyridin-2(3H)-one-3,2'-benzo[e]indan],
spiro[imidazo[2,1-a]isoquinolin-2(3H)-one-3,1'-(3'-cyclopentene)],
spiro[8-benzyloxyimidazo[1,2-a]pyridin-2(3H)-one-3,1'-(3'-cyclopentene)],
spiro[7,8,9,10-tetrahydroimidazo[2,1-a]isoquinolin-2(3H)-one-3,1'-cyclopentane],
spiro[imidazo[2,1-a]isoquinolin-2(3H)-one-3,1'-cyclopentane], and spiro[5,6,7,8-tetrahydroimidazo[1,2-a]pyridin-2(3H)-one-3, 2'-indan]

The heterocyclic compound of Formula (I) can be in the form of hydrate or acid addition salts as a pharmaceutically acceptable salt. Possible acid addition salts include inorganic acid salts such as the hydrochloride, sulfate, hydrobromide, nitrate, and phosphate salts and organic acid salts such as acetate, oxalate, propionate, glycolate, lactate, pyruvate, malonate, succinate, maleate, fumarate, malate, tartrate, citrate, benzoate, cinnamate, methanesulfonate, benzenesulfonate, p-toluenesulfonate, and salicylate salts.

The administration method, formulation, and dosage of the heterocyclic compound in mammals, particularly in human, are described hereafter. The heterocyclic compound can be administrated orally or parenterally. Formulations for oral administration include tablets, coated tablets, powder, granules, capsules, microcapsules, and syrups. Formulations for parenteral administration include injectable solutions (including those freeze-dried and dissolved for use), adhesive skin patches, and suppositories.

These formulations can be prepared using pharmaceutically acceptable fillers, binders, lubricants, disintegrators, suspending agents, emulsifiers, antiseptic agents, stabilizing agents, and dispersing agents such as lactoses, saccharoses, starches, dextrines, crystalline celluloses, kaolins, calcium carbonate, talc, magnesium stearate, and distilled water or saline. Particular pharmaceutically acceptable components include mannitol, mircocrystalline cellulose, hydroxypropyl cellulose, and magnesium stearate. The dosage varies according to the symptom, age, and body weight of patients. An adult can take 0.1 to 100 mg per day in one to three doses.

In one embodiment, the invention provides an antidepressant composition comprising a compound of the general Formula (I).

The inventors found that heterocyclic compounds having Formula I exhibit antidepressant activity in forced swimming test and tail suspension test as described later in examples. Screening of the compounds for antidepressant activity showed thatazaindolizinone derivatives in which a dibenzyl group or an indan ring forms a spiro ring have potent antidepressant activity. These compounds exhibit antidepressant activity based on a novel mechanism that does not involve the inhibition of serotonin reuptake. The compound spiro[imidazo[1,2-a]pyridin-2(3H)-one-3,2'-indan] has also been shown to be highly safe in a preclinical study.

The antidepressant of this embodiment exhibits excellent antidepressant effect. More specifically, the antidepressant of this embodiment inhibits one or more mood disorders selected from the group consisting of depression, manic depressive psychoses, obsessive-compulsive disorder, panic disorder, and anxiety disorder in mammals. The heterocyclic compound contained in the antidepressant composition of this embodiment is preferably among the compounds below because these compounds have been shown to have excellent antidepressive activity in the mouse tail suspension test, which is a typical test for antidepressive activity of a compound in a mouse model.

3,3-dibenzylimidazo[1,2-a]pyridin-2(3H)-one,
spiro[imidazo[1,2-a]pyridin-2(3H)-one-3,2'-indan],
3,3-dipropylimidazo[1,2-a]pyridin-2(3H)-one, 3,3-dibutyl-imidazo[1,2-a]pyridin-2(3H)-one,
5,5-dibenzylimidazo[2,1-b]thiazol-6(5H)-one, 3,3-dibenzylimidazo[1,2-a]pyrimidin-2(3H)-one,
spiro[imidazo[1,2-a]pyridin-2(3H)-one-3,2'-(4'-fluoroindan)],
spiro[imidazo[1,2-a]pyridin-2(3H)-one-3,2'-(4'-cyanoindan)],
spiro[imidazo[2,1-a]isoquinolin-2(3H)-one-3,2'-indan],
spiro[imidazo[1,2-a]pyridin-2(3H)-one-3,2'-((1,2,5-thiadiazo)[4,5-c]indan)],
spiro[imidazo[1,2-a]pyrimidin-2(3H)-one-3,2'-indan],
spiro[imidazo[2,1-a]isoquinolin-2(3H)-one-3,4'-(1'-cyclopentene)],
3,3-bis(4-chlorobenzyl)imidazo[1,2-a]pyridin-2(3H)-one,
8-cyclopropylmethyloxy-3,3-diallylimidazo[1,2-a]pyridin-2(3H)-one,
spiro[imidazo[1,2-a]pyridin-2(3H)-one-3,2'-(4'-hydroxy-indan)],
spiro[8-hydroxy-imidazo[1,2-a]pyridin-2(3H)-one-3,2'-indan],
spiro[8-methoxy-imidazo[1,2-a]pyridin-2(3H)-one-3,4'-(1'-cyclopentene)], and
spiro[8-cyclopropylmethyloxyimidazo[1,2-a]pyridin-2(3H)-one-3,4'-(1'-cyclopentene)].

The antidepressant compound may be administered by a means which acheives reduction or alleviation of depression in a mammal. In one embodiment, the antidepressant compound is orally administered. In another embodiment, the antidepressant is administered as part of an adhesive skin patch. Alternatively, the antidepressant compound is formulated into tablets, coated tablets, powder, granules, capsules, microcapsules, and syrups. The antidepressant in the form of oral formulations is easily administered to mammals, including human beings.

The antidepressant compound may be administered at an effective oral dosage of 0.0005 mg per kilogram of body weight or higher, more preferably 0.005 mg per kilogram of body weight or higher, and particularly preferably 0.05 mg per kilogram of body weight or higher. In one embodiment, the compound is administered as part of a unitary pharmaceutical dosage form containing 5, 10, 15, 20, 25, 30, 35, 40, 45, 50, 55, 60, 65, 70, 75, 80, 85, 90, 95, or 100 mg. When the antidepressant compound is administered at an effective oral dosage of these lower limits or higher, the antidepressive activity in mammals including human beings is improved compared to when lower doses are administered.

In another embodiment, the invention provides a neuroprotectant composition comprising a compound of Formula (I)

The inventors found spiro[imidazo[1,2-a]pyridin-2(3H)-one-3,2'-indan] within Formula (I) exhibits neuroprotective activity in a study on reduction in delayed neuronal death in the hippocampus CA1 field in the gerbil transient forbrain ischemia model as described later in examples. Screening of derivatives of the above compound for neuroprotective activity showed that azaindolizinone derivatives in which an indan ring forms a spiro ring have potent neuroprotective activity. The above compound exhibits neuroprotective activity based on a novel mechanism different from antioxidization.

spiro[imidazo[1,2-a]pyridin-2(3H)-one-3,2'-indan] has also been shown to be highly safe in the preclinical study.

The neuroprotectant composition containing the compound of Formula (I), in particular, spiro[imidazo[1,2-a]pyridin-2(3H)-one-3,2'-indan], is effective at lower dosages based on a mechanism different from that of Edaravone, which is a neuroprotectant having antioxidative activity. Therefore, the neuroprotectant composition is expected to avoid various side effects such as kidney failure as reported for Edaravone.

The neuroprotectant composition of this embodiment exhibits excellent neuroprotective activity. In one embodiment, the composition inhibit one or more cerebrovascular disorders selected from the group consisting of transient ischemic attack, cerebral hemorrhage, subarachnoid hemorrhage, intracranial hemorrhage, cerebral infarct, and hypertensive encephalopathy in mammals.

The neuroprotectant compound of this embodiment is preferably spiro[imidazo[1,2-a]pyridin-2(3H)-one-3,2'-indan]. This compound was shown to have an excellent neuroprotective activity in a study on reduction in delayed neuronal death in the hippocampus CA1 region in the gerbil transient forebrain ischemia model, which is a typical animal model for neuroprotection, as described later in the examples.

The neuroprotectant compound may be administered by a means which provides neuroprotection in a mammal. Preferably, the neuroprotectant compound of this embodiment is orally administered. In another embodiment, the neuroprotectant compound can be administered as part of an adhesive skin patch. The neuroprotectant compound may be formulated into tablets, coated tablets, powder, granules, capsules, microcapsules, and syrups. The neuroprotectant in the form of oral formulations is easily administered in mammals, including human beings.

The neuroprotectant compound may be administered at an effective oral dosage of 0.005 mg per kilogram body weight or higher, more preferably 0.05 mg per kilogram of body weight or higher, and particularly preferably 0.5 mg per kilogram of body weight or higher. When the neuroprotectant compound is administered at an effective oral dosage of these lower limits or higher, the neuroprotective activity in mammals including human beings is improved compared to when lower doses are administered.

In another embodiment, the invention provides an amyloid β deposition inhibitor composition comprising a compound having Formula (I).

The inventors found that a compound of Formula (I), in particular, spiro[imidazo[1,2-a]pyridin-2(3H)-one-3,2'-indan], exhibits inhibitory activity of amyloid β deposition in the hippocampus by amyloid β immunohistochemistry as described later in the examples. Screening of derivatives of the compound for amyloid β deposition inhibitory activity showed that azaindolizinone derivatives in which an indan ring forms a spiro ring have potent amyloid β deposition inhibitory activity. The above compound exhibits amyloid β deposition inhibitory activity based on a novel mechanism different from antioxidative activity. The compound has also been shown to be highly safe in the preclinical study.

The amyloid β deposition inhibitor of Formula (I), in particular, spiro[imidazo[1,2-a]pyridin-2(3H)-one-3,2'-indan], is effective at lower dosages based on a mechanism which is different from curcumin, a component of *Curcuma longa* contained in curry in a large amount and which has antioxidative activity. Therefore, it is a new amyloid β deposition inhibitor having a mechanism of action different from curcumin.

The amyloid β deposition inhibitor of Formula (I), in particular, spiro[imidazo[1,2-a]pyridin-2(3H)-one-3,2'-indan], exhibits excellent inhibitory activity of amyloid β deposition. More specifically, the amyloid deposition inhibitor of Formula (I) inhibits one or more amyloid-related pathologies selected from the group consisting of amyloidosis, cerebral amyloid angiopathy, cataract, glaucoma, the progression of glaucoma, age-related macular degeneration, rheumatism, osteoporosis, metabolic syndrome, wrinkles, and hair loss in mammals.

The amyloid β deposition inhibitor of this embodiment is preferably spiro[imidazo[1,2-a]pyridin-2(3H)-one-3,2'-indan] as this compound was shown to have excellent inhibitory activity of amyloid β deposition in the hippocampus amyloid β immunohistochemistry, which is a typical animal model test for inhibitory activity of amyloid β deposition, as described later in the examples.

The amyloid β deposition inhibitor compound may be administered by any means which acheives reduction in amyloid β deposition in a mammal. Preferably, the amyloid β deposition inhibitor compound of this embodiment is orally administered. In another embodiment, the amyloid β deposition inhibitor compound may be administered as part of an adhesive skin patch. Alternatively, the amyloid deposition inhibitor compound may be formulated into tablets, coated tablets, powder, granules, capsules, microcapsules, and syrups, as the amyloid deposition inhibitor in the form of oral formulations is easily administered in mammals, including human beings.

The amyloid β deposition inhibitor compound of this embodiment is preferably administered at an effective oral dosage of 0.0005 mg per kilogram of body weight or higher. In one embodiment, the compound is administered as part of a unitary pharmaceutical dosage form containing 5, 10, 15, 20, 25, 30, 35, 40, 45, 50, 55, 60, 65, 70, 75, 80, 85, 90, 95, or 100 mg. When the amyloid β deposition inhibitor is administered at an effective oral dosage of this lower limit or higher, the amyloid β deposition inhibitory activity in mammals including human beings is improved compared to when lower doses are administered.

In another embodiment, the invention provides an age retardant composition comprising a compound of general Formula (I). The invention also provides a composition comprising a compound of general Formula (I) for delaying senescence in an animal in need thereof, comprising administering to the animal an effective amount of a heterocyclic compound having the general Formula (I). In one embodiment, the composition comprising a compound of general Formula (I) improves and/or delays in worstening symptoms of one or more conditions associated with senescence, including reactivity, passivity, glossiness and/or coarseness of hair, hair loss, ulcers, periophthalmic lesions, cataracts, corneal opacity and lordokyphosis. In another embodiment, the invention provides the composition comprising a compound of general Formula (I) for extending the life span of a mammal in need thereof, comprising administering to the mammal an effective amount of a compound having the general Formula (I).

The inventors found that the compound of Formula (I), in particular, spiro[imidazo[1,2-a]pyridin-2(3H)-one-3,2'-indan], exhibits age retardant activity in measurement of grading scores in senescene accelerated mice as described later in the examples. Screening of compounds for age retardant activity showed that azaindolizinone derivatives in which an indan ring forms a spiro ring have potent age retardant activity. The above compound exhibits age retardant activity based on a novel mechanism which is different from an antioxidative activity. Spiro[imidazo[1,2-a]pyridin-2(3H)-one-3,2'-indan] has also been shown to be highly safe in a preclinical study.

The age retardant compound of this embodiment is effective at lower dosages based on a mechanism which is different from oolong tea and deprenyl, both having antioxidative activity. Therefore, it is a new age retardant having a mechanism different from oolong tea and deprenyl. In other words, the compound of Formula (I) can be used as an antiaging drug having a novel mechanism which is different from those drugs having antioxidative activity. It is expected that the compound of Formula (I) will have an age retardant activity with improved efficacy at lower dosages compared to oolong tea and deprenyl.

The age retardant compound of this embodiment exhibits excellent age retardant activity. The age retardant compound of this embodiment slows down the aging process in mice and is expected to slow the aging process in other mammals including human beings. The age retardant compound also extends the average life span in mice and is expected to extend the average life span in other mammals including human beings.

The age retardant compound of this embodiment is preferably spiro[imidazo[1,2-a]pyridin-2(3H)-one-3,2'-indan] as this compound was shown to have excellent age retardant activity in measurement of grading scores in senescene accelerated mice, which is an animal model for age retardant activity, as described later in examples. Furthermore, this compound was shown to extend the average life span in senescene accelerated mice as described later in examples.

The age retardant compound may be administered by any means which achieves delaying of scenescence in a mammal. Preferably, the age retardant compound of this embodiment is orally administered. In another embodiment, the age retardant compound can be administered as part of an adhesive skin patch. The age retardant compound may be formulated into tablets, coated tablets, powder, granules, capsules, microcapsules, and syrups, as the age retardant compound in the form of oral formulations is easily administered to mammals, including human beings.

The age retardant compound of this embodiment is preferably administered at an effective oral dosage of 0.0005 mg per kilogram of body weight or higher, more preferably 0.005 mg per kilogram of body weight or higher, and particularly preferably 0.05 mg per kilogram of body weight or higher. In one embodiment, the compound is administered as part of a unitary pharmaceutical dosage form containing 5, 10, 15, 20, 25, 30, 35, 40, 45, 50, 55, 60, 65, 70, 75, 80, 85, 90, 95, or 100 mg. When the age retardant is administered at an effective oral dosage of these lower limits or higher, the age retardant activity in mammals including human beings is improved compared to when lower doses are administered.

The age retardant compound is preferably administered at an effective oral dosage of 0.005 mg per kilogram of body weight or higher for extended average life span. When the age retardant compound is administered at an effective oral dosage of this lower limit or higher, the average life span is extended in mammals including human beings.

Embodiments of the present invention are described above. These embodiments are given by way of example. The present invention can be realized in many other ways as the invention is not so limited.

For example, some preferable ranges of effective oral dosages are defined in the above embodiments. However, other ranges of effective dosages can be determined for other administration forms. For example, a preferable range of effective dosages for administration by injection can be determined as appropriate. Furthermore, preferable ranges of administration intervals can be determined for particular administration forms in addition to the effective dosages with no more than routine experimentation.

EXAMPLES

The present invention is further described using examples. However, the present invention is not restricted thereto.

Example 1

Antidepressant Activity

In order to prove the antidepressant activity of the heterocyclic compound having the specific structure described in Embodiment 1, a tail suspension test was conducted on ICR mice (male). First, one hour after oral dosing of 0.001, 0.01, and 0.1 mg/kg of a subject compound, the mice were clipped by the tail approximately 1 cm from the tip, suspended, and observed for 6 minutes. Motionless time was measured in the last 4 minutes. The antidepressant activity was considered to be positive when 90 seconds or less motionless time was observed.

TABLE 1

| compound | dosage (mg/kg, p.o) | time (sec) |
| --- | --- | --- |
| Compound 10 | 0.001 | 72.8 |
| Compound 24 | 0.001 | 72.8 |
| Compound 29 | 0.01 | 61.3 |
| Compound 34 | 0.001 | 83.3 |
| Compound 44 | 0.1 | 88 |
| Compound 45 | 0.001 | 89.5 |
| Compound 56 | 0.001 | 88.3 |
| Compound 59 | 0.01 | 86.3 |
| Compound 60 | 0.1 | 79.5 |
| Compound 61 | 0.01 | 82 |
| Compound 63 | 0.001 | 73 |
| Compound 69 | 0.001 | 58.5 |
| Compound 78 | 0.01 | 68.5 |
| Compound 79 | 0.001 | 66.5 |
| Compound 80 | 0.1 | 64.3 |
| Compound 81 | 0.001 | 86.3 |
| Compound 82 | 0.01 | 81.8 |
| Compound 83 | 0.001 | 78 |
| Solvent Control | | 113.2 |

As shown above, all compounds were considered to have antidepressant activity because of 90 seconds or less motionless time in the mice tail suspension test was observed. In other words, compounds having Formula I were shown to have antidepressant activity. The structures and names of the above compounds are given in Exemplary Preparations described later.

Example 2

Neuroprotective Activity

In order to prove neuroprotection activity of compounds having Formula I, the activity of Compound 24 on reduction in delayed neuronal death in the hippocampus CA1 region in the gerbil transient forbrain ischemia model was examined.

Gerbils (male, weighing approximately 55 to 80 g) were pinched with an exposed bilateral common carotid artery by microclip to cause the cerebral ischemia under 2% halothane inhalation anesthesia. After four minutes of ischemia, the microclip was removed to reperfuse the cerebral ischemia and the anesthesia was stopped. Four days after the reperfusion, the brain was removed and formalin-fixed. Sections of 4 μm in thickness were prepared and stained with hematoxylin-eosin. Surviving cells in the entire hippocampus CA1 field on both sides of each specimen were counted using a micrometer under the microscope. The number of surviving cells per 0.5 mm was obtained.

Compound 24 was suspended in 1% HPC and orally given one hour before the cerebral ischemia and 5 hours after the reperfusion. Then, two doses per day were given from the following day to the third day since the perfusion. The surviving cell count in the hippocampus CA1 field was expressed by the average±standard error. The Mann-Whitney's U test was used to obtain significant differences. The effective oral dosage of Compound 24 was plotted as abscissa and the surviving cell count/0.5 mm was plotted as ordinate.

The surviving cell count in the hippocampus CA1 field of a sham surgery group (n=7) was 117.3±2.3/0.5 mm. On the other hand, the surviving cell count of the solvent control group (n=7) was 18.1±1.0/0.5 mm; significant reduction in number of surviving cells, namely onset of delayed neuronal death, in the hippocampus CA1 field through the cerebral ischemia—reperfusion was observed.

FIG. 1 is a graphical representation for explaining the hippocampus CA1 field protection activity of Compound 24 in the gerbil transient forebrain ischemia model. In FIG. 1, ** indicates p<0.01 vs the control.

Figure 2:
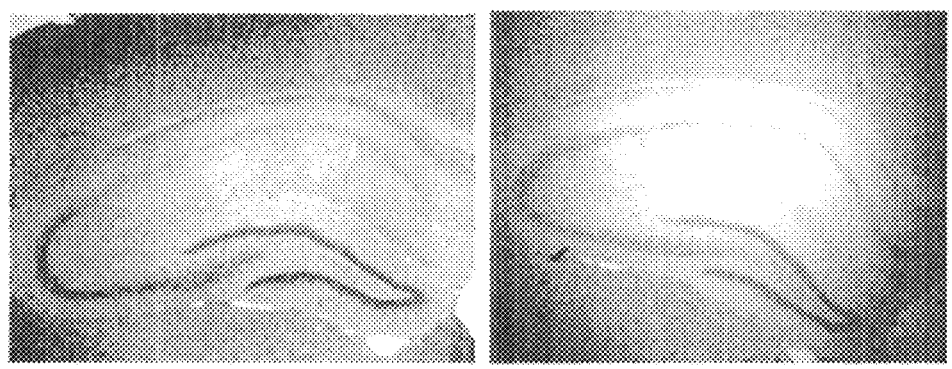
FIG. 2 contains photographs for explaining the neuroprotective activity in delayed neuronal death in the hippocampus CA1 region in the gebil transient forebrain ischemia model.

FIG. 2 is photographs for explaining the neuroprotective activity in delayed neuronal death in the hippocampus CA1 region in the gerbil transient forbrain ischemia model. The left photograph shows the case no Compound 24 was given and the right photograph shows the case Compound 24 was given.

When Compound 24 was given at an oral dosage of 0.001 to 20 mg/kg, the number of surviving cells in the hippocampus CA1 field was dosage-dependently and significantly increased (**) in the dosage groups of 0.01 mg/kg (n=7), 0.1 mg/kg (n=8), and 1 mg/kg (n=9) as shown in FIGS. 1 and 2 (the surviving cell counts: 0.01 mg/kg; 27.8±1.9/0.5 mm, 0.1 mg/kg; 32.5±9.4/0.5 mm, 1 mg/kg: 44.3±9.4/0.5 mm).

From the above results, Compound 24 was shown to reduce neuronal death and be an effective neuroprotectant. Hence, Compound 24 is expected to be effective as a neuroprotectant for cerebrovascular disorders such as transient ischemic attack, cerebral hemorrhage, subarachnoid hemorrhage, intracranial hemorrhage with cerebral arteriovenous malformation, cerebral infarct, and hypertensive encephalopathy.

As described above, a compound having Formula (I) was shown to have neuroprotective activity in a study on reduction in delayed neuronal death in the hippocampus CA1 field in the gerbil transient forebrain ischemia model.

Example 3

Amyloid β Deposition Inhibitory Activity

In order to show that compounds having Formula (I) have amyloid β deposition inhibitory activity, the activity of Compound 24 on amyloid β deposition was examined.

Senescene accelerated mice (SAMP8) (male, 8 months old at the beginning of the study) were used for experiment. Approximately 0.1 mg/kg/day of Compound 24 was given in drinking water. Eight weeks after the dosing, the mouse brain was removed, Methacarn-fixed (methanol:chloroform: acetic acid=6:3:1), and paraffin-embedded. Then, sections of 8 μm in thickness were prepared using a microtome.

The sections were immunostained with streptavidin-biotin using a VECTASTATIN ABC kit. After one hour of incubation in 10% normal goat serum, the anti-amyloid β (Aβ) antibody was diluted with PBS to ten fold and incubated at 4° C. overnight. The following day, PBS rinsing, 1.5 hours of incubation with biotinylated anti-rabbit secondary antibody, PBS rinsing, and 1.5 hours of incubation with peroxidase-labeled streptavidin were conducted. The immunoreaction was visualized with DAB and specimens were prepared.

Immunoreactive Aβ-like granules in the hippocampus were counted under the microscope. The Aβ-like immunoreactive granule was observed as brown deposits in the hippocampus. The count was made for one section per individual.

Figure 3:
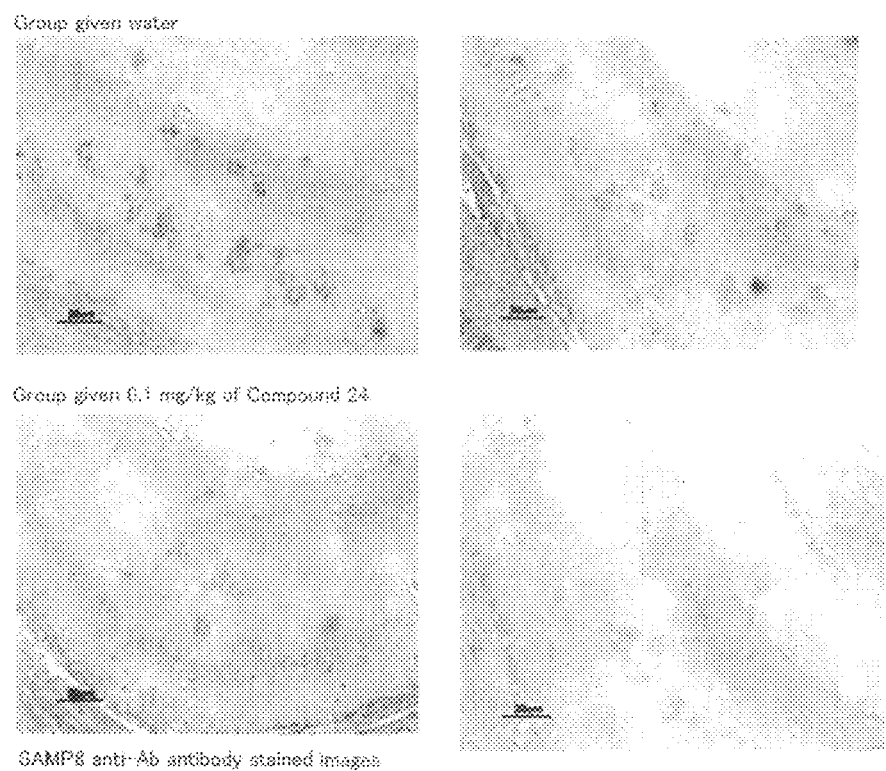
FIG. 3 contains photographs for explaining the effect of Compound 24 on the number of amyloid β-immunoreactive cells in senescene accelerated mice (SAMP8).

FIG. 3 contains photographs showing the influence of Compound 24 on the number of amyloid β-immunoreactive cells in senescene accelerated mice (SAMP8). The photographs at the top show stained images of amyloid β-like granules in the hippocampus of senescene accelerated mice (SAMP8) given tap water as drinking water for 2 months from age of 8 months. The photographs at the bottom show stained images of amyloid β-like immunoreactivity in the hippocampus of senescene accelerated mice (SAMP8) given Compound 24 in drinking water at an effective oral dosage of 0.1 mg per kilogram of body weight for 2 months.

Figure 4:
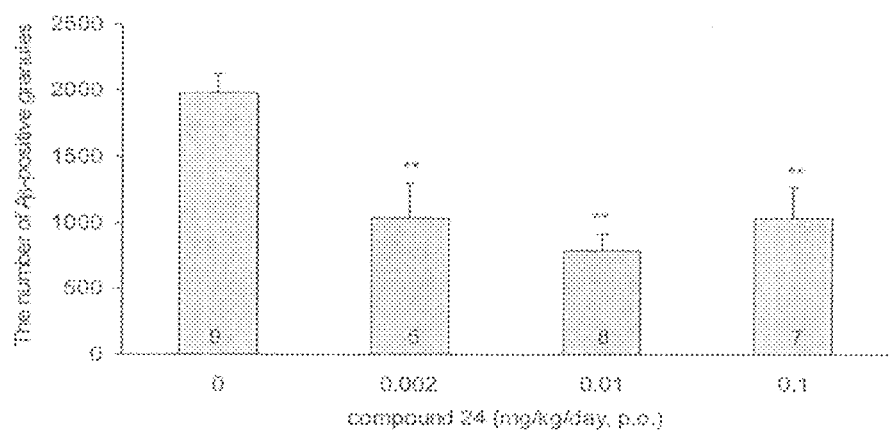
FIG. 4 depicts a graphical representation for explaining the effect of Compound 24 on the number of amyloid β-immunoreactive cells in senescene accelerated mice (SAMP8).

FIG. 4 is a graphical representation showing the influence of Compound 24 on the number of amyloid β-immunoreactive cells in senescene accelerated mice (SAMP8). The effective oral dosage of Compound 24 is plotted as abscissa and the number of amyloid β-immunoreactive granules is plotted as ordinate. Nine senescene accelerated mice (SAMP8) were given no Compound 24. Five, eight and seven senescene accelerated mice (SAMP8) were given Compound 24 at oral dosage of 0.002 mg, 0.01 mg and 0.1 mg per kilogram of body weight respectively.

As shown in FIGS. 3 and 4, an amyloid β-like immunoreactivity in the hippocampus was observed in senescene accelerated mice (SAMP8) given tap water as drinking water for 2 months from age of 8 months. On the other hand, the amyloid (3-like immunoreactivity was reduced in senescene accelerated mice (SAMP8) given Compound 24 in drinking water at oral dosage of 0.002 mg/kg/day, 0.01 mg/kg/day and 0.1 mg/kg/day for 2 months. The number of amyloid β-immunoreactive granules was significantly (*) decreased as a result of dosing of Compound 24.

As described above, Compound 24 inhibits amyloid β deposition. Amyloid-related pathologies for which Compound 24 may be used include cataract, glaucoma, the progression of glaucoma, age-related macular degeneration, rheumatism, osteoporosis, metabolic profiling syndrome, wrinkles, and hair loss, in which amyloid β is considered to be a factor of the disorder. Compound 24 inhibits amyloid β deposition and, therefore, may also be used for to treat amyloidosis or cerebral amyloid angiopathy, which are characterized by amyloid fibrillates and deposits.

As described above, a compound having Formula (I) was shown to have inhibitory activity of amyloid β deposition in an amyloid β immunohistochemistry.

Example 4

Age Retardant Activity

In order to show that compounds having Formula (I) have age retardant activity, a study was conducted on the effect of Compound 24 on prevention of fur deterioration and extension of the average life span in senescene accelerated mice (SAM).

Senescene accelerated mice (SAMP8) (male, 8 months old at the beginning of the study) were used in the study.

Compound 24 dissolved in tap water was given to the senescene accelerated mice at a dosage of 0.001, 0.01, or 0.1 mg/kg/day as drinking water. Tap water was given to the control mice as drinking water.

As an aging indicator of senescene accelerated mice, grading scores (Takeda et al., 1981) were measured after 0, 4, 8, 12, and 16 weeks of drinking water dosing in a short term study and after 12, 16, 20, 24, 28, and 32 weeks of drinking water dosing in a long term study.

Figure 5:
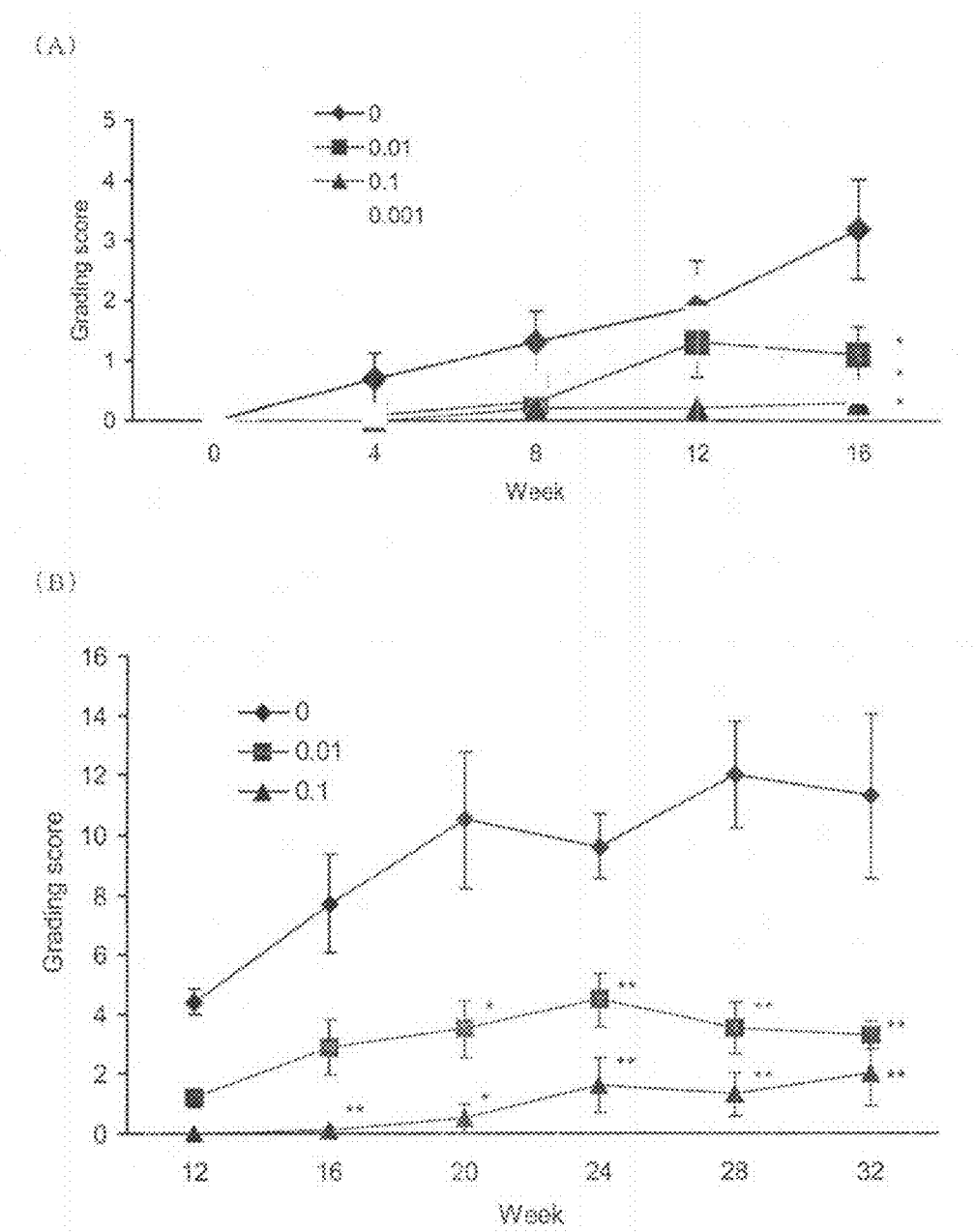
FIG. 5 depicts a graphical representation for explaining the effect of Compound 24 on the grading scores in senescene accelerated mice (SAMP8).

FIG. 5 is a graphical representation showing the influence of Compound 24 on the grading scores in senescene accelerated mice (SAMP8). FIG. 5 (A) shows the results of the short term study and FIG. 5 (B) shows the results of the long term study. In both figures, the number of weeks of dosing is plotted as abscissa and the grading score is plotted as ordinate.

As seen from the results, as shown in FIG. 5 (A), the grading score as an aging indicator started increasing after Week 12 of the drinking water dosing in senescene accelerated mice (SAMP8) given water while the grading score did not increase in senescene accelerated mice (SAMP8) given Compound 24 in drinking water. Significant differences (*) in this activity were observed in Week 16 in the groups given Compound 24 in drinking water at effective oral dosages of 0.001, 0.01, and 0.1 mg/kg/day. The difference was notable in the group given Compound 24 in drinking water at effective oral dosage of 0.1 mg/kg/day.

As shown in FIG. 5 (B), the group given Compound 24 in drinking water at an effective oral dosage of 0.01 mg/kg/day exhibited significant differences (*, **) in Weeks 20 to 32. The group given Compound 24 in drinking water at an effective oral dosage of 0.1 mg/kg/day exhibited significant differences (*, **) in Weeks 16 to 32. The results show that Compound 24 significantly prevented the aging in senescene accelerated mice (SAMP8).

Figure 6:
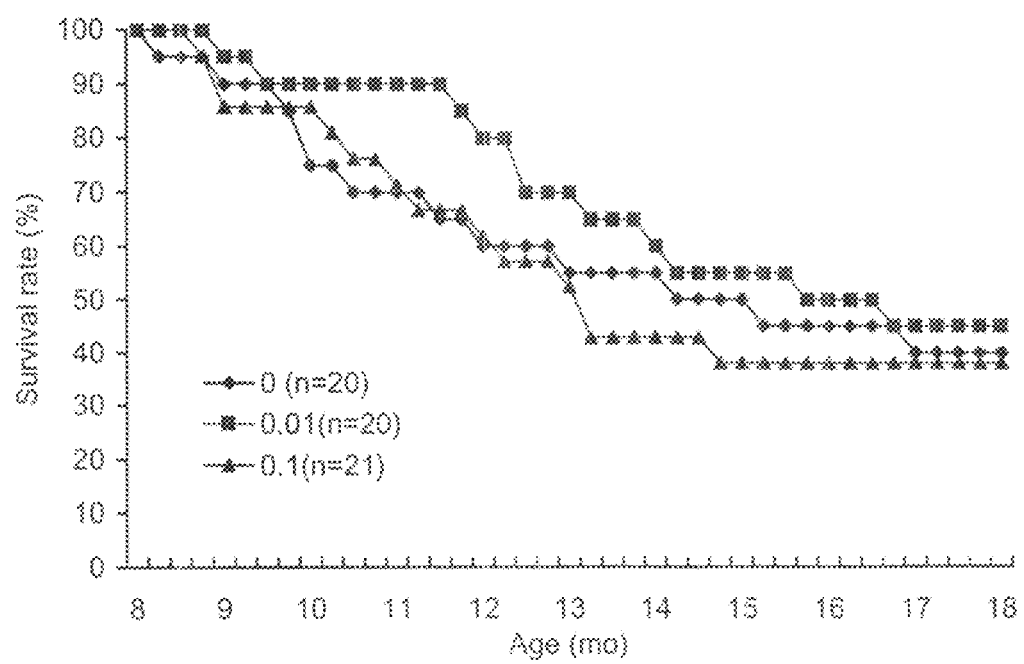
FIG. 6 depicts a graphical representation for explaining the effect of Compound 24 on the survival rate of senescene accelerated mice (SAMP8).

FIG. 6 is a graphical representation showing the influence of Compound 24 on the survival rate of senescene accelerated mice (SAMP8). The age in months of mice is plotted as abscissa and the survival rate (%) is plotted as ordinate.

The results in FIG. 6 show that the average life span was extended in the group given Compound 24 in drinking water at an effective oral dosage of 0.01 mg/kg/day at any age in month compared to the control group of senescene accelerated mice (SAMP8) given tap water. Hence, Compound 24 was shown to extend the average life span in senescene accelerated mice (SAMP8).

As described above, a compound of Formula (I) was shown to have age retardant activity and extend the average life expectancy in a study of Compound 24 on prevention of fur deterioration and extension of the average life span in senescene accelerated mice (SAM).

Preparation of Compounds Referred to in the Embodiments

Some of the heterocyclic compound having the general Formula (I) and prepared by the method in examples of Booklet of International Publication No. 01/09131 are described hereafter by way of example. More specifically, they were synthesized with reference to Booklet of International Publication No. 01/09131 and Booklet of International Publication No. 2002/060907 Brochure.

Exemplary Preparation 1

An exemplary preparation of 3,3-dibenzyl-8-isopropoxy-imidazo[1,2-a]pyridin-2(3H)-one (Compound 1) having the general formula below is described hereafter.

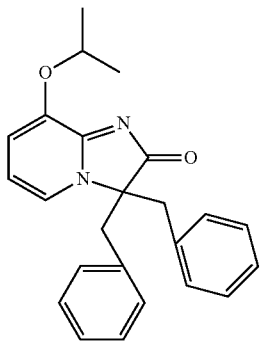

An amount of 81 mg of metallic sodium was added to 3.0 ml of absolute ethanol and stirred at room temperature for one hour. An amount of 586 mg (1.77 mmol) of 2-amino-3-isopropoxy-1-(ethoxycarbonylmethyl)pyridinium bromide was added and further stirred at room temperature for one hour. Then, 605 mg (3.54 mmol) of benzyl bromide was added to the reaction mixture at 0° C. and stirred at room temperature for four hours. The precipitated crystals were filtered off and dried. The obtained crystals were recrystallized from ethanol to yield 588 mg of the title compound (yield: 92%).

Results of analysis of the obtained compound are given below. The results show that the obtained compound was the targeted compound.

Melting Point: 247-248 DC;

NMR (CDCl$_3$) δ: 1.03 (6H, d, J=6 Hz), 3.15 (2H, d, J=14 Hz), 3.56 (2H, d, J=14 Hz), 4.60 (1H, sept., J=6 Hz), 6.48 (1H, t, J=7 Hz), 6.79 (1H, d, J=8 Hz), 6.9-7.2 (11H, m);

MS m/z: 372 (M$^+$)

Exemplary Preparation 2

Compounds 2 to 40 of Formulae (I) were each prepared from the respective starting materials in the same manner as in Exemplary Preparation 1. Results of analysis of the obtained compounds are given for each compound. The results show that the obtained compounds were the targeted Compounds 2 to 40.

3,3-dibenzyl-8-methoxyimidazo[1,2-a]pyridin-2(3H)-one (Compound 2)

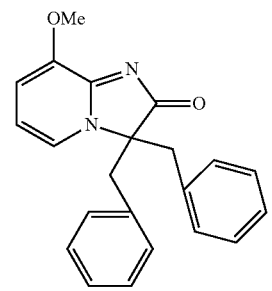 [SMILES: COC1=CC=CN2C1=NC(=O)C2(Cc1ccccc1)Cc1ccccc1]

Melting Point: 274-275° C.;

NMR (CDCl$_3$) δ: 3.17 (2H, d, J=14 Hz), 3.56 (2H, d, J=14 Hz), 3.69 (3H, s), 6.49 (1H, t, J=7 Hz), 6.67 (1H, d, J=8 Hz), 6.9-7.2 (11H, m);

MS m/z: 344 (M$^+$).

3,3-dibenzyl-8-cyclopropylmethyloxy-imidazo[1,2-a]pyridin-2(3H)-one (Compound 3)

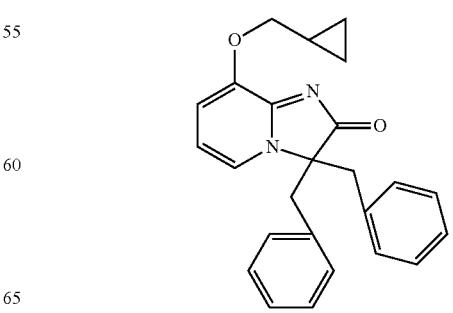

Melting Point: 236-237° C.;
NMR (CDCl$_3$) δ: 0.12 (2H, q, J=5 Hz), 0.45 (2H, q, J=6 Hz), 0.99 (1H, m), 3.16 (2H, d, J=14 Hz), 3.55 (2H, d, J=14 Hz), 3.73 (2H, d, J=7 Hz), 6.47 (1H, t, J=7 Hz), 6.76 (1H, d, J=8 Hz), 7.0-7.2 (11H, m);
MS m/z: 384 (M$^+$).

3,3-dibenzyl-6-chloroimidazo[1,2-a]pyridin-2(3H)-one (Compound 4)

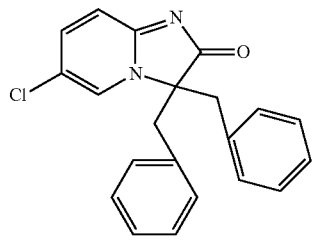 [SMILES: O=C1N=C2C=CC(Cl)=CN2C1(Cc1ccccc1)Cc1ccccc1]

Melting Point: 246-248° C.;
NMR (CDCl$_3$) δ: 3.16 (2H, d, J=14 Hz), 3.55 (2H, d, J=14 Hz), 6.70 (1H, d, J=10 Hz), 7.0-7.2 (12H, m);
MS m/z: 348 (M$^+$).

8-allyloxy-3,3-dibenzylimidazo[1,2-a]pyridin-2(3H)-one (Compound 5)

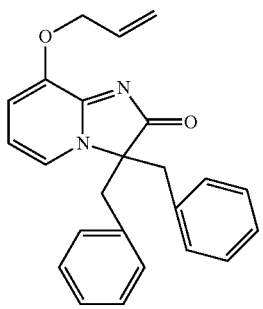 [SMILES: C=CCOC1=CC=CN2C1=NC(=O)C2(Cc1ccccc1)Cc1ccccc1]

Melting Point: 214-215° C.;
NMR (CDCl$_3$) δ: 3.16 (2H, d, J=14 Hz), 3.56 (2H, d, J=14 Hz), 4.4-4.5 (2H, m), 5.0-5.2 (2H, m), 5.7-5.9 (1H, m), 6.47 (1H, t, J=7 Hz), 6.74 (1H, d, J=8 Hz), 6.9-7.2 (11H, m);
MS m/z: 370 (M$^+$).

3,3-dibenzyl-8-benzyloxyimidazo[1,2-a]pyridin-2(3H)-one (Compound 6)

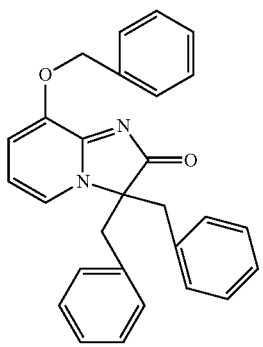 [SMILES: O=C1N=C2C(OCc3ccccc3)=CC=CN2C1(Cc1ccccc1)Cc1ccccc1]

Melting Point: 240-241° C.;
NMR (CDCl$_3$) δ: 3.17 (2H, d, J=14 Hz), 3.57 (2H, d, J=14 Hz), 5.03 (2H, s), 6.39 (1H, t, J=8 Hz), 6.65 (1H, d, J=8 Hz), 7.0-7.2 (16H, m);
MS m/z: 420 (M$^+$).

8-benzyloxy-3,3-bis(1-phenylethyl)imidazo[1,2-a]pyridin-2(3H)-one (Compound 7)

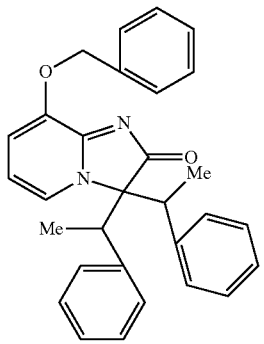 [SMILES: CC(c1ccccc1)C1(C(C)c2ccccc2)C(=O)N=C2C(OCc3ccccc3)=CC=CN21]

Melting Point: 234-235° C.;
NMR (CDCl$_3$) δ: 1.52 (6H, d, J=7 Hz), 3.51 (2H, q, J=7 Hz), 5.11 (2H, s), 6.14 (1H, t, J=7 Hz), 6.41 (1H, d, J=7 Hz), 6.63 (1H, d, J=8 Hz), 7.0-7.2 (15H, m);
MS m/z: 448 (M$^+$).

3,3-dibenzyl-8-methylimidazo[1,2-a]pyridin-2(3H)-one (Compound 8)

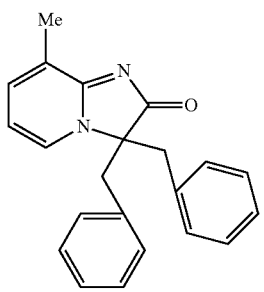 [SMILES: CC1=CC=CN2C1=NC(=O)C2(Cc1ccccc1)Cc1ccccc1]

Melting Point: 262-263° C.;
NMR (CDCl$_3$) δ: 2.05 (3H, s), 3.31 (2H, d, J=14 Hz), 3.56 (2H, d, J=14 Hz), 6.60 (1H, t, J=7 Hz), 6.9-7.2 (12H, m);
MS m/z: 328 (M$^+$).

3,3-dibenzyl-5,7-dimethylimidazo[1,2-a]pyridin-2(3H)-one (Compound 9)

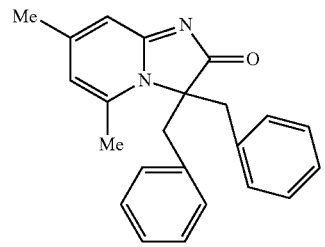 [SMILES: CC1=CC2=NC(=O)C(Cc3ccccc3)(Cc3ccccc3)N2C(C)=C1]

Melting Point: 237-238° C.;
NMR (CDCl$_3$) δ: 2.07 (3H, s), 2.80 (3H, s), 3.40 (2H, d, J=15 Hz), 3.71 (2H, d, J=15 Hz), 6.11 (1H, s), 6.34 (1H, s), 7.0-7.2 (10H, m);
MS m/z: 342 (M$^+$).

3,3-dibenzylimidazo[1,2-a]pyridin-2(3H)-one (Compound 10)

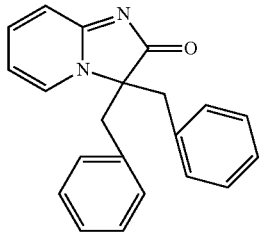 [SMILES: O=C1N=C2C=CC=CN2C1(Cc1ccccc1)Cc1ccccc1]

Melting Point: >300° C.;

NMR (DMSO-D6) δ: 3.39 (4H, s), 6.60 (1H, d, J=9 Hz), 6.8-7.2 (11H, m), 7.56 (1H, t, J=71-Iz), 8.75 (1H, d, J=7 Hz);

MS m/z: 314 (M⁺).

3,3-dibenzyl-8-cyclopentyloxyimidazo[1,2-a]pyridin-2(3H)-one (Compound 11)

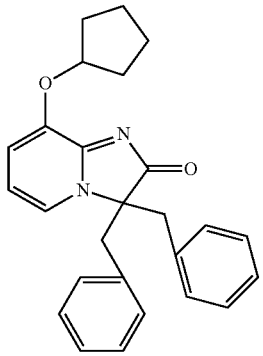 [SMILES: O=C1N=C2C(OC3CCCC3)=CC=CN2C1(Cc1ccccc1)Cc1ccccc1]

Melting Point: 268-269° C.;

NMR (CDCl₃) δ: 1.4-1.7 (8H, m), 3.15 (2H, d, J=14 Hz), 3.55 (1H, d, J=14 Hz), 4.7-4.9 (1H, m), 6.47 (1H, t, J=7 Hz), 6.72 (1H, d, J=8 Hz), 6.9-7.2 (11H, m);

MS m/z: 398 (M⁺).

3,3-dibenzyl-6,8-dichloroimidazo[1,2-a]pyridin-2(3H)-one (Compound 12)

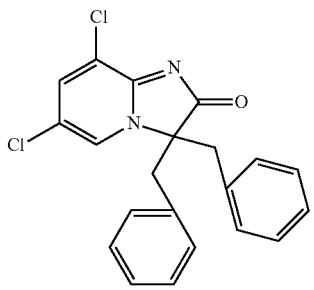 [SMILES: O=C1N=C2C(Cl)=CC(Cl)=CN2C1(Cc1ccccc1)Cc1ccccc1]

Melting Point: 260-261° C.;

NMR (CDCl₃) δ: 3.17 (2H, d, j=14 Hz), 3.55 (2H, d, J=14 Hz), 6.9-7.3 (11H, m), 7.41 (1H, d, J=2 Hz);

MS m/z: 382 (M⁺).

3,3-dibenzyl-8-chloro-6-trifluoromethylimidazo[1,2-a]pyridin-2(3H)-one (Compound 13)

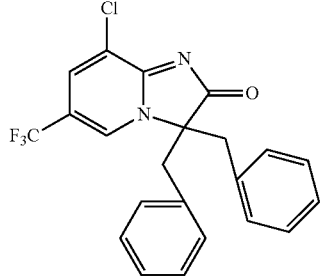 [SMILES: O=C1N=C2C(Cl)=CC(C(F)(F)F)=CN2C1(Cc1ccccc1)Cc1ccccc1]

Melting Point: 234-236° C.;

NMR (CDCl₃) δ: 3.22 (2H, d, J=14 Hz), 3.55 (2H, d, J=14 Hz), 6.9-7.0 (4H, m), 7.1-7.4 (7H, m), 7.51 (1H, d, J=2 Hz);

MS m/z: 416 (M⁺).

8-benzyloxy-3,3-bis(3-methylbenzyl)imidazo[1,2-a]pyridin-2(3H)-one (Compound 14)

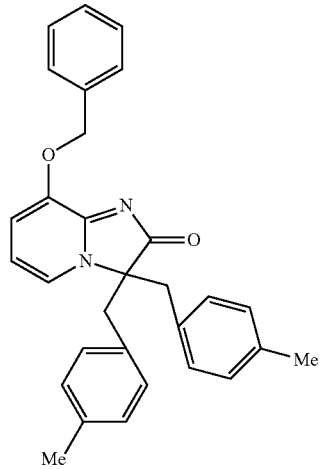 [SMILES: Cc1ccc(CC2(Cc3ccc(C)cc3)C(=O)N=C3C(OCc4ccccc4)=CC=CN32)cc1]

Melting Point: 233-235° C.;

NMR (CDCl₃) δ: 2.20 (6H, s), 3.14 (2H, d, J=14 Hz), 3.48 (2H, d, J=14 Hz), 5.05 (2H, s), 6.38 (1H, t, J=7 Hz), 6.68 (1H, d, J=8 Hz), 6.7-7.3 (14H, m);

MS m/z: 448 (M⁺).

8-methyl-3,3-bis(4-pyridylmethyl)imidazo[1,2-a]pyridin-2(3H)-one (Compound 15)

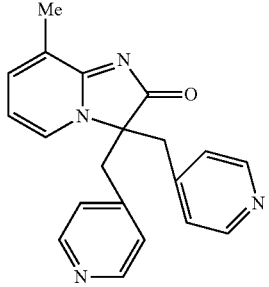 [SMILES: CC1=CC=CN2C1=NC(=O)C2(Cc1ccncc1)Cc1ccncc1]

Melting Point: 228-230° C.;

NMR (CDCl₃) δ: 2.01 (3H, s), 3.13 (2H, d, J=14 Hz), 3.60 (2H, d, J=14 Hz), 6.60 (1H, t, J=7 Hz), 6.95 (4H, d, J=6 Hz), 7.22 (1H, d, J=7 Hz), 7.46 (1H, d, J=7 Hz), 8.40 (4H, d, J=6 Hz);

MS m/z: 330 (M⁺).

3,3-bis(4-fluorobenzyl)imidazo[1,2-a]pyridin-2(3H)-one (Compound 16)

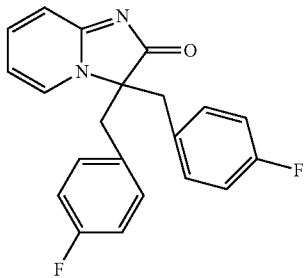 [SMILES: O=C1N=C2C=CC=CN2C1(Cc1ccc(F)cc1)Cc1ccc(F)cc1]

Melting Point: 290-292° C.;

NMR (CDCl$_3$) δ: 3.13 (2H, d, J=14 Hz), 3.56 (2H, d, J=14 Hz), 6.62 (1H, t, J=7 Hz), 6.7-6.9 m), 6.9-7.1 (4H, m), 7.39 (1H, t, J=7 Hz), 7.52 (1H, brd, J=7 Hz);

MS m/z: 350 (M$^+$).

3,3-bis(4-dimethylaminobenzyl)imidazo[1,2-a]pyridin-2(3H)-one (Compound 17)

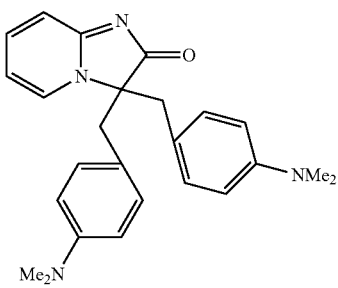 [SMILES: CN(C)c1ccc(CC2(Cc3ccc(N(C)C)cc3)C(=O)N=C3C=CC=CN32)cc1]

Melting Point: >300° C.;

NMR (CDCl$_3$) δ: 2.86 (12H, s), 3.09 (2H, d, J=14 Hz), 3.37 (2H, d, J=14 Hz), 6.4-6.6 (5H, m), 6.7-6.9 (5H, m), 7.2-7.3 (1H, m), 7.37 (1H, t, J=7 Hz);

MS m/z: 400 (M$^+$).

3,3-bis(3-chlorobenzyl)imidazo[1,2-a]pyridin-2(3H)-one (Compound 18)

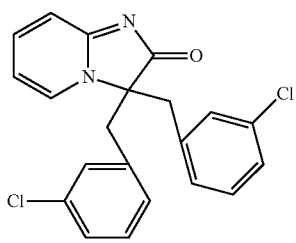 [SMILES: O=C1N=C2C=CC=CN2C1(Cc1cccc(Cl)c1)Cc1cccc(Cl)c1]

Melting Point: 271-272° C.;

NMR (CDCl$_3$) δ: 3.14 (2H, d, J=14 Hz), 3.53 (2H, d, J=14 Hz), 6.66 (1H, t, J=7 Hz), 6.80 (1H, d, J=7 Hz), 6.9-7.2 (8H, m), 7.43 (1H, t, J=7 Hz), 7.51 (1H, brd, J=7 Hz);

MS m/z: 382 (M$^+$).

3,3-bis(4-methoxybenzyl)imidazo[1,2-a]pyridin-2(3H)-one (Compound 19)

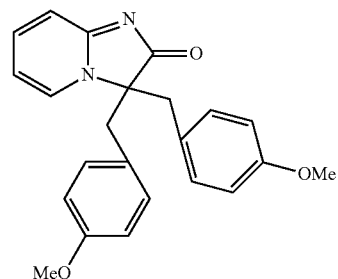 [SMILES: COc1ccc(CC2(Cc3ccc(OC)cc3)C(=O)N=C3C=CC=CN32)cc1]

Melting Point: 248-251° C.;

NMR (CDCl$_3$) δ: 3.66 (6H, s), 3.67 (2H, d, J=15 Hz), 4.00 (2H, d, J=15 Hz), 6.59 (4H, d, J=9 Hz), 6.93 (4H, d, J=9 Hz), 7.50 (1H, t, J=7 Hz), 6.71 (1H, d, J=7 Hz), 7.91 (1H, t, J=7 Hz), 9.78 (1H, d, J=7 Hz);

MS m/z: 374 (M$^+$).

3,3-bis(4-biphenylmethyl)imidazo[1,2-a]pyridin-2(3H)-one (Compound 20)

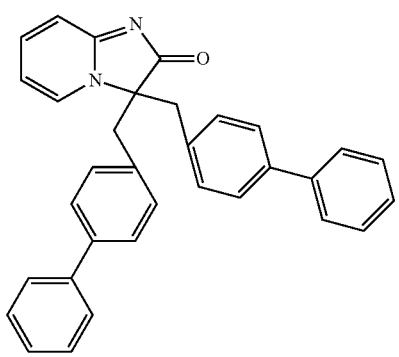 [SMILES: O=C1N=C2C=CC=CN2C1(Cc1ccc(-c2ccccc2)cc1)Cc1ccc(-c2ccccc2)cc1]

Melting Point: >300° C.;

NMR (CDCl$_3$) δ: 3.25 (2H, d, J=14 Hz), 3.62 (2H, d, J=14 Hz), 6.58 (1H, t, J=7 Hz), 6.77 d, J=7 Hz), 7.11 (4H, d, J=7 Hz), 7.3-7.6 (16H, m);

MS m/z: 466 (M$^+$).

3,3-bis(4-cyanobenzyl)imidazo[1,2-a]pyridin-2(3H)-one (Compound 21)

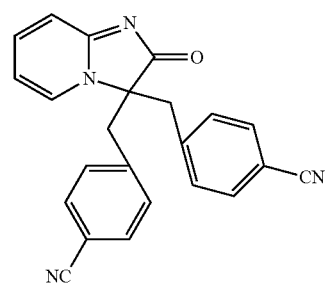 [SMILES: N#Cc1ccc(CC2(Cc3ccc(C#N)cc3)C(=O)N=C3C=CC=CN32)cc1]

Melting Point: 294° C. (decomposition);

NMR (CDCl$_3$) δ: 3.19 (2H, d, J=14 Hz), 3.70 (2H, d, J=14 Hz), 6.6-6.8 (2H, m), 7.13 (4H, d, J=7 Hz), 7.43 (1H, t, J=7 Hz), 7.45 (4H, d, J=7 Hz), 7.62 (1H, brd, J=7 Hz);

MS m/z: 364 (M$^+$).

3,3-bis(4-hydroxybenzyl)imidazo[1,2-a]pyridin-2(3H)-one (Compound 22)

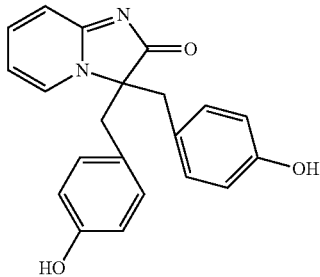 [SMILES: O=C1N=C2C=CC=CN2C1(Cc1ccc(O)cc1)Cc1ccc(O)cc1]

Melting Point: 276.5-277.5° C.;
NMR (CD$_3$OD-CDCl$_3$(1:1)) δ: 3.62 (2H, d, J=14 Hz), 3.66 (2H, d, J=14 Hz), 6.58 (4H, d, J=9 Hz), 6.78 (4H, d, J=9 Hz), 7.17 (1H, d, J=7 Hz), 7.63 (1H, t, J=7 Hz), 8.12 (1H, t, J=7 Hz), 9.25 (1H, d, J=7 Hz);
MS m/z: 346 (M$^+$).

3,3-diallylimidazo[1,2-a]pyridin-2(3H)-one (Compound 23)

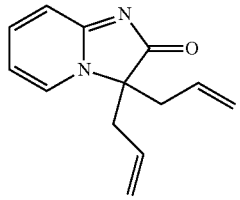 [SMILES: C=CCC1(CC=C)C(=O)N=C2C=CC=CN21]

Melting Point: 64-66° C.;
NMR (CDCl$_3$) δ: 2.56 (2H, dd, J=9 Hz, J=14 Hz), 2.86 (2H, dd, J=6 Hz, J=14 Hz), 4.99 (2H, dd, J=1 Hz, J=7 Hz), 5.04 (2H, d, J=1 Hz), 5.4-5.6 (2H, m), 6.67 (1H, t, J=7 Hz), 7.17 (1H, d, J=7 Hz), 7.52 (1H, d, J=7 Hz), 7.59 (1H, d, J=7 Hz);
MS m/z: 214 (M$^+$).

spiro[imidazo[1,2-a]pyridin-2(3H)-one-3,2'-indan] (Compound 24)

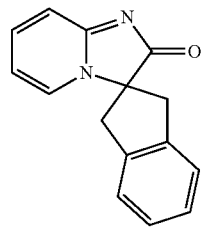 [SMILES: O=C1N=C2C=CC=CN2C12Cc1ccccc1C2]

Melting Point: 206° C. (decomposition);
NMR (CDCl$_3$) δ: 3.16 (2H, d, J=16 Hz), 3.89 (2H, d, J=16 Hz), 6.49 (1H, t, J=7 Hz), 7.1-7.2 (2H, m), 7.2-7.3 (4H, m), 7.61 (1H, t, J=7 Hz);
MS m/z: 236 (M$^+$).

3,3-diallyl-8-benzyloxyimidazo[1,2-a]pyridin-2(3H)-one (Compound 25)

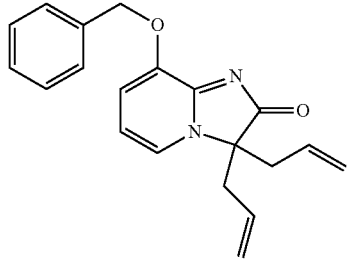 [SMILES: C=CCC1(CC=C)C(=O)N=C2C(OCc3ccccc3)=CC=CN21]

Melting Point: 160-162° C.;
NMR (CDCl$_3$) δ: 2.54 (2H, dd, J=8 Hz, J=14 Hz), 2.86 (2H, dd, J=6 Hz, J=14 Hz), 4.96 (2H, dd, J=1 Hz, J=5 Hz), 5.01 (2H, d, J=1 Hz), 5.29 (2H, s), 5.4-5.6 (2H, m), 6.53 (1H, dd, J=7 Hz, J=8 Hz), 6.94 (1H, d, J=7 Hz), 7.16 (1H, d, J=8 Hz), 7.3-7.5 (5H, m);
MS m/z: 320 (M$^+$).

3,3-bis(3-phenyl-1-propyl)imidazo[1,2-a]pyridin-2(3H)-one (Compound 26)

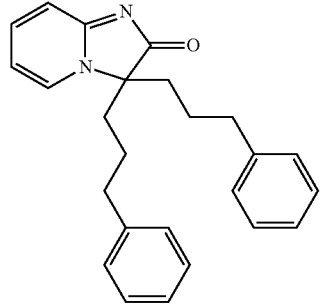 [SMILES: O=C1N=C2C=CC=CN2C1(CCCc1ccccc1)CCCc1ccccc1]

Melting Point: 227-228° C.;
NMR (CDCl$_3$) δ: 0.9-1.1 (2H, m), 1.4-1.6 (2H, m), 1.6-1.8 (2H, m), 2.0-2.2 (2H, m), 2.3-2.5 (2H, m), 2.5-2.7 (2H, m), 6.61 (1H, t, J=7 Hz), 7.0-7.1 (4H, m), 7.1-7.3 (8H, m), 7.58 (1H, t, J=7 Hz);
MS m/z: 370 (M$^+$).

spiro[imidazo[1,2-a]pyridin-2(3H)-one-3,2'-[2,3]-dihydrophenarene] (Compound 27)

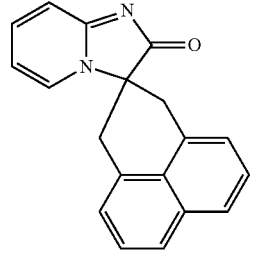 [SMILES: O=C1N=C2C=CC=CN2C12Cc1cccc3cccc(c13)C2]

Melting Point: 262° C. (decomposition);
NMR (CDCl$_3$): 3.12 (2H, d, J=17 Hz), 3.98 (2H, d, J=17 Hz), 6.18 (1H, t, J=7 Hz), 6.48 (1H, d, J=7 Hz), 7.24 (1H, d, J=7 Hz), 7.34 (1H, d, J=7 Hz), 7.4-7.6 (3H, m), 7.86 (2H, d, J=7 Hz);
MS m/z: 286 (M$^+$).

3,3-bis(2,4-difluorobenzyl)imidazo[1,2-a]pyridin-2(3H)-one (Compound 28)

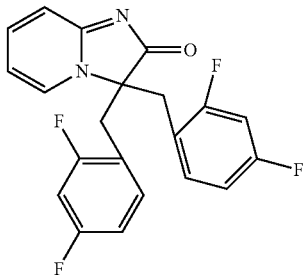 [SMILES: O=C1N=C2C=CC=CN2C1(Cc1ccc(F)cc1F)Cc1ccc(F)cc1F]

Melting Point: 269-271° C.;
NMR (CDCl$_3$) δ: 3.38 (2H, d, J=14 Hz), 3.47 (2H, d, J=14 Hz), 6.5-6.7 (3H, m), 6.7-6.8 (3H, m), 7.2-7.5 (3H, m), 7.6-7.7 (1H, m);
MS m/z: 368 (M$^+$).

3,3-dipropylimidazo[1,2-a]pyridin-2(3H)-one (Compound 29)

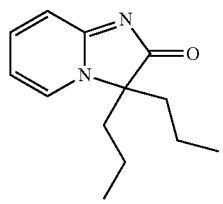 [SMILES: CCCC1(CCC)C(=O)N=C2C=CC=CN21]

Melting Point: 73-75° C.;
NMR (CDCl$_3$) δ: 0.7-0.9 (8H, m), 1.1-1.3 (2H, m), 1.6-1.8 (2H, m), 2.0-2.2 (2H, m), 6.73 (1H, t, J=7 Hz), 7.19 (1H, d, J=7 Hz), 7.50 (1H, d, J=7 Hz), 7.63 (1H, t, J=7 Hz);
MS m/z: 218 (M$^+$).

3,3-bis(2-thienylmethyl)imidazo[1,2-a]pyridin-2(3H)-one (Compound 30)

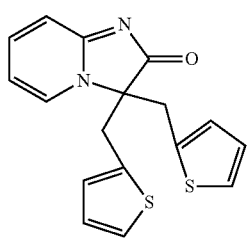 [SMILES: O=C1N=C2C=CC=CN2C1(Cc1cccs1)Cc1cccs1]

Melting Point: 289.5° C. (decomposition);
NMR (CDCl$_3$) δ: 3.41 (2H, d, J=15 Hz), 3.70 (2H, d, J=15 Hz), 6.64 (1H, t, J=7 Hz), 6.7-7.0 (5H, m), 7.07 (2H, dd, J=1 Hz, J=5 Hz), 7.38 (1H, d, J=7 Hz), 7.48 (1H, t, J=7 Hz);
MS m/z: 326 (M$^+$).

8-acetylamino-3,3-dibenzylimidazo[1,2-a]pyridin-2(3H)-one (Compound 31)

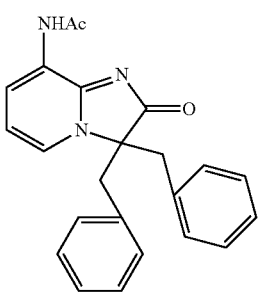 [SMILES: CC(=O)NC1=CC=CN2C1=NC(=O)C2(Cc1ccccc1)Cc1ccccc1]

Melting Point: 235-237° C.;
NMR (CDCl$_3$) δ: 2.05 (3H, s), 3.20 (2H, d, J=14 Hz), 3.55 (2H, d, J=14 Hz), 6.61 (1H, t, J=7 Hz), 6.9-7.1 (4H, m), 7.1-7.2 (7H, m), 7.78 (1H, brs), 8.39 (1H, d, J=7 Hz);
MS m/z: 371 (M$^+$).

3,3-bis(2-furylmethyl)imidazo[1,2-a]pyridin-2(3H)-one (Compound 32)

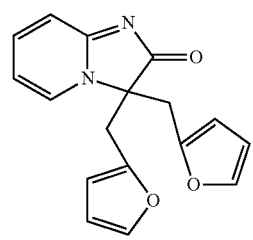 [SMILES: O=C1N=C2C=CC=CN2C1(Cc1ccco1)Cc1ccco1]

Melting Point: 205° C. (decomposition);
NMR (CDCl$_3$) δ: 3.37 (4H, s), 6.11 (2H, d, J=3 Hz), 6.23 (2H, dd, J=2 Hz, J=3 Hz), 6.56 (1H, t, J=7 Hz), 6.97 (1H, d, J=7 Hz), 7.20 (2H, d, J=2 Hz), 7.22 (1H, d, J=7 Hz), 7.51 (1H, t, J=7 Hz);
MS m/z: 294 (M$^+$).

3,3-dimethylimidazo[1,2-a]pyridin-2(3H)-one (Compound 33)

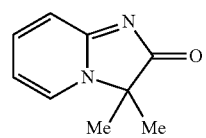 [SMILES: CC1(C)C(=O)N=C2C=CC=CN21]

Melting Point: 200-202° C.;
NMR (CD$_3$OD-CDCl$_3$(1:1)) δ: 1.93 (6H, s), 7.72 (1H, t, J=7 Hz), 7.78 (1H, d, J=7 Hz), 8.50 (1H, t, J=7 Hz), 9.01 (1H, d, J=7 Hz);
MS m/z: 162 (M$^+$).

3,3-dibutylimidazo[1,2-a]pyridin-2(3H)-one (Compound 34)

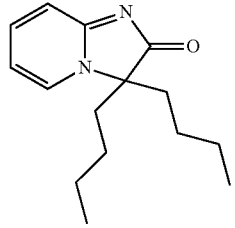 [SMILES: CCCCC1(CCCC)C(=O)N=C2C=CC=CN21]

Melting Point: 100.5-102° C.;

NMR (CDCl$_3$) δ: 0.6-0.9 (8H, m), 1.0-1.3 (6H, m), 1.6-1.8 (2H, m), 2.0-2.2 (2H, m), 6.71 (1H, t, J=7 Hz), 7.19 (1H, d, J=7 Hz), 7.50 (1H, d, J=7 Hz), 7.62 (1H, t, J=7 Hz);

MS m/z: 246 (M$^+$).

3,3-di(2-propinyl)imidazo[1,2-a]pyridin-2(3H)-one (Compound 35)

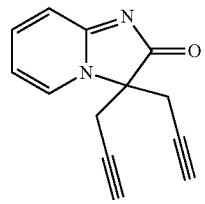 [SMILES: C#CCC1(CC#C)C(=O)N=C2C=CC=CN21]

Melting Point: 172-175° C.;

NMR (CDCl$_3$) δ: 2.07 (2H, t, J=3 Hz), 2.80 (2H, dd, J=3 Hz, J=17 Hz), 3.08 (2H, dd, J=2.6 Hz, J=17 Hz), 6.75 (1H, t, J=7 Hz), 7.24 (1H, d, J=7 Hz), 7.69 (1H, t, J=7 Hz), 8.02 (1H, d, J=7 Hz);

MS m/z: 210 (M$^+$).

3,3-dibenzyl-8-hydroxyimidazo[1,2-a]pyridin-2(3H)-one (Compound 36)

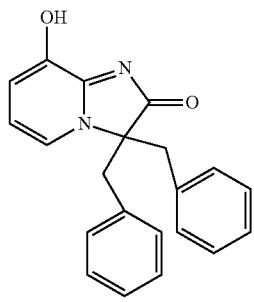 [SMILES: O=C1N=C2C(O)=CC=CN2C1(Cc1ccccc1)Cc1ccccc1]

Melting Point: 283-285° C.;

NMR (CDCl$_3$) δ: 3.20 (2H, d, J=14 Hz), 3.55 (2H, d, J=14 Hz), 6.58 (1H, t, J=7 Hz), 6.87 (1H, d, J=7 Hz), 6.9-7.0 (4H, m), 7.07 (1H, d, J=7 Hz), 7.1-7.2 (6H, m);

MS m/z: 330 (M$^+$).

3,3-dibenzyl-8-benzylaminoimidazo[1,2-a]pyridin-2(3H)-one (Compound 37)

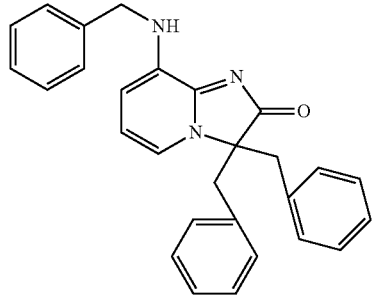 [SMILES: O=C1N=C2C(NCc3ccccc3)=CC=CN2C1(Cc1ccccc1)Cc1ccccc1]

Melting Point: 250° C.;

NMR (CDCl$_3$) δ: 3.42 (2H, d, J=14 Hz), 3.70 (2H, d, J=14 Hz), 4.35 (2H, d, J=6 Hz), 6.93 (1H, d, J=7 Hz), 7.0-7.3 (16H, m), 7.48 (1H, d, J=7 Hz), 8.66 (1H, brs);

MS m/z: 419 (M$^+$).

3,3-bis(4-nitrobenzyl)imidazo[1,2-a]pyridin-2(3H)-one (Compound 38)

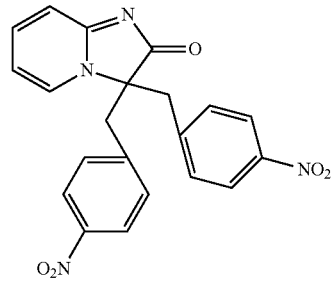 [SMILES: O=C1N=C2C=CC=CN2C1(Cc1ccc([N+](=O)[O-])cc1)Cc1ccc([N+](=O)[O-])cc1]

Melting Point: >300° C.;

NMR (CD$_3$OD-CDCl$_3$(1:1)) δ: 3.21 (2H, d, J=14 Hz), 3.67 (2H, d, J=14 Hz), 6.66 (1H, t, J=7 Hz), 6.75 (1H, d, J=7 Hz), 7.15 (4H, d, J=9 Hz), 7.39 (1H, t, J=7 Hz), 7.42 (4H, d, J=9 Hz), 7.56 (1H, d, J=7 Hz);

MS m/z: 404 (M$^+$).

8-amino-3,3-dibenzylimidazo[1,2-a]pyridin-2(3H)-one (Compound 39)

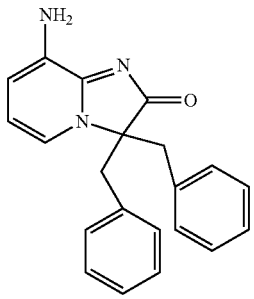 [SMILES: NC1=CC=CN2C1=NC(=O)C2(Cc1ccccc1)Cc1ccccc1]

Melting Point: 283-285° C.;

NMR (CDCl$_3$) δ: 3.17 (2H, d, J=14 Hz), 3.53 (2H, d, J=14 Hz), 4.06 (2H, brs), 6.4-6.5 (2H, m), 6.94 (1H, t, J=7 Hz), 7.0-7.1 (4H, m), 7.1-7.2 (6H, m);

MS m/z: 330 (M$^+$).

3,3-bis(4-methoxycarbonylbenzyl)imidazo[1,2-a]pyridin-2(3H)-one (Compound 40)

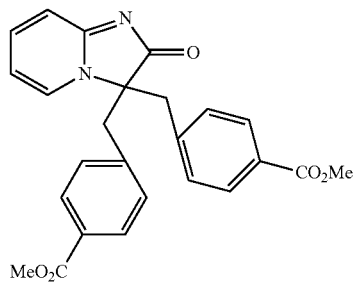 [SMILES: COC(=O)c1ccc(CC2(Cc3ccc(C(=O)OC)cc3)C(=O)N=C3C=CC=CN32)cc1]

Melting Point: 289-290° C.;

NMR (CDCl$_3$) δ: 3.22 (2H, d, J=14 Hz), 3.66 (2H, d, J=14 Hz), 3.86 (6H, s), 6.60 (1H, t, J=7 Hz), 6.70 (1H, d, J=7 Hz), 7.0-7.1 (4H, m), 7.35 (1H, t, J=7 Hz), 7.50 (1H, d, J=7 Hz), 7.8-7.9 (4H, m);

MS m/z: 430 (M$^+$).

Exemplary Preparation 3

An exemplary preparation of 5,5-bis(4-fluorobenzyl)imidazo[2,1-b]thiazol-6(5H)-one (Compound 43) having the general formula below is described hereafter.

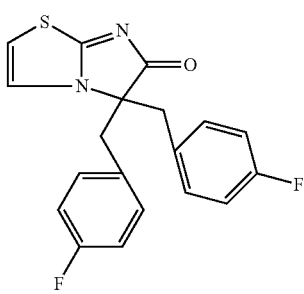

First, 300 mg (1.4 mmol) of 2-amino-3-ethoxycarbonylmethylthiazolium bromide and then 1.15 ml (9.0 mmol) of p-fluorobenzyl bromide were added to an ethanol solution (10 ml) of sodium ethoxide prepared from 210 mg (9.0 mmol) of metallic sodium while cooling over ice and stirred at room temperature overnight. The solvent was removed by distillation under reduced pressure and water was added to the residue. The resultant mixture was extracted several times using ethyl acetate, rinsed with saturated brine, and dried over anhydrous magnesium sulfate. The solvent was removed by distillation under reduced pressure and the residue was chromatographed over silica gel column (ethyl acetate:methanol=10:1). An amount of 852 mg (80.0%) of the title compound was obtained in the form of crystals. Recrystallization from ethanol yielded white crystals having a melting point of higher than 300° C.

Results of analysis of the obtained compound are given below. The results show that the obtained compound was the targeted compound.

NMR (CD$_3$OD-CDCl$_3$(1:1)) δ: 3.23 (2H, d, J=14 Hz), 3.43 (2H, d, J=14 Hz), 6.66 (1H, d, J=4 Hz), 6.8-6.9 (4H, m), 6.9-7.1 (4H, m), 7.28 (1H, d, J=4 Hz);

MS m/z: 356 (M$^+$).

Exemplary Preparation 4

Compounds 44 to 68 having the general formulae corresponding to starting materials were each prepared in the same manner as in Exemplary Preparation 3. Results of analysis of the obtained compounds are given below. The results show the obtained compounds were the targeted compounds.

5,5-dibenzylimidazo[2,1-b]thiazol-6(5H)-one (Compound 44)

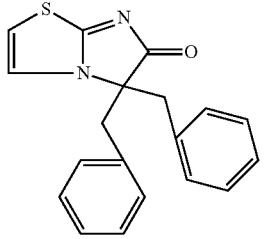 [SMILES: O=C1N=C2SC=CN2C1(Cc1ccccc1)Cc1ccccc1]

Melting Point: >300° C.;

NMR (DMSO-d$_6$) δ: 3.69 (2H, d, J=15 Hz), 3.74 (2H, d, J=15 Hz), 7.27 (1H, d, J=4 Hz), 7.3-7.4 (4H, m), 7.5-7.6 (6H, m), 8.44 (1H, d, J=4 Hz);

MS m/z: 320 (M$^+$).

3,3-dibenzylimidazo[1,2-a]pyrimidin-2(3H)-one (Compound 45)

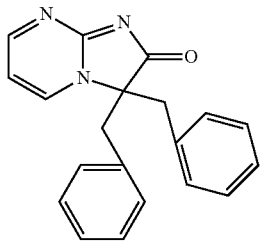 [SMILES: O=C1N=C2N=CC=CN2C1(Cc1ccccc1)Cc1ccccc1]

Melting Point: >300° C.;

NMR (DMSO-d$_6$) δ: 3.42 (4H, dd, J=14 Hz, J=16 Hz), 6.9-7.0 (5H, m), 7.1-7.2 (6H, m), 8.46 (1H, dd, J=3 Hz, J=5 Hz), 9.07 (1H, dd, J=2 Hz, J=6 Hz);

MS m/z: 315 (M$^+$).

5,5-bis(4-methylbenzyl)imidazo[2,1-b]thiazol-6(5H)-one (Compound 46)

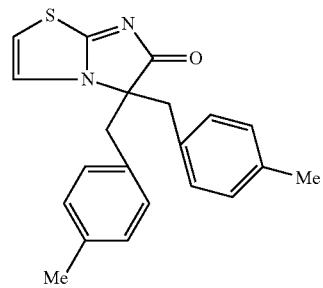 [SMILES: Cc1ccc(CC2(Cc3ccc(C)cc3)C(=O)N=C3SC=CN32)cc1]

Melting Point: >300° C.;

NMR (DMSO-d$_6$) δ: 2.20 (6H, s), 3.24 (2H, d, J=14 Hz), 3.36 (2H, d, J=14 Hz), 6.84 (4H, d, J=8 Hz), 6.89 (1H, d, J=4 Hz), 6.97 (4H, d, J=8 Hz), 8.03 (4H, d, J=4 Hz);

MS m/z: 348 (M$^+$).

5,5-bis(4-cyanobenzyl)imidazo[2,1-b]thiazol-6(5H)-one (Compound 47)

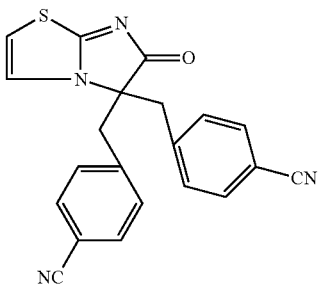 [SMILES: N#Cc1ccc(CC2(Cc3ccc(C#N)cc3)C(=O)N=C3SC=CN32)cc1]

Melting Point: 264-267° C.;

NMR (CDCl$_3$) δ: 3.23 (2H, d, J=14 Hz), 3.56 (2H, d, J=14 Hz), 6.54 (1H, d, J=6 Hz), 7.02 (1H, d, J=6 Hz), 7.15 (4H, d, J=9 Hz), 7.51 (4H, d, J=9 Hz);

MS m/z: 370 (M$^+$).

5,5-dibenzyl-2-methylimidazo[2,1-b]thiazol-6(5H)-one (Compound 48)

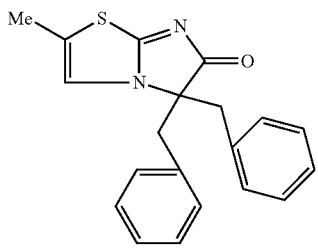 [SMILES: CC1=CN2C(=NC(=O)C2(Cc2ccccc2)Cc2ccccc2)S1]

Melting Point: >300° C.;

NMR (CD$_3$OD-CDCl$_3$ (1:1)) δ: 2.34 (3H, d, J=1 Hz), 3.28 (2H, d, J=13 Hz), 3.43 (2H, d, J=13 Hz), 7.0-7.1 (4H, m), 7.1-7.3 (7H, m);

MS m/z: 334 (M$^+$).

5,5-bis(2-thienylmethyl)imidazo[2,1-b]thiazol-6(5H)-one (Compound 49)

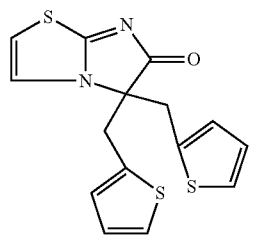 [SMILES: O=C1N=C2SC=CN2C1(Cc1cccs1)Cc1cccs1]

Melting Point: 286° C. (decomposition);

NMR (CDCl$_3$) or 3.43 (2H, d, J=15 Hz), 3.60 (2H, d, J=15 Hz), 6.49 (1H, d, J=5 Hz), 6.7-7.0 (5H, m), 7.12 (2H, dd, J=1 Hz, J=6 Hz);

MS m/z: 332 (M$^+$).

3,3-bis(2-thienylmethyl)imidazo[1,2-a]pyrimidin-2(3H)-one (Compound 50)

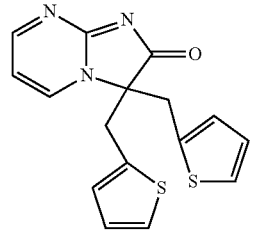 [SMILES: O=C1N=C2N=CC=CN2C1(Cc1cccs1)Cc1cccs1]

Melting Point: 192° C. (decomposition);

NMR (CD$_3$OD-CDCl$_3$(1:1)) δ: 3.54 (2H, d, J=15 Hz), 3.76 (2H, d, J=15 Hz), 6.7-6.9 (5H, m), 7.11 (2H, dd, J=1 Hz, J=5 Hz), 8.23 (1H, dd, J=2 Hz, J=6 Hz), 8.62 (1H, dd, J=2 Hz, J=4 Hz);

MS m/z: 327 (M$^+$).

5,5-dibenzyl-2,3-dihydroimidazo[2,1-b]thiazol-6(5H)-one (Compound 51)

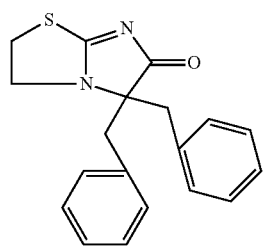 [SMILES: O=C1N=C2SCCN2C1(Cc1ccccc1)Cc1ccccc1]

Melting Point: 233-236° C.;

NMR (CDCl$_3$) 3.0:3 (2H, d, J=14 Hz), 3.23 (2H, t, J=7 Hz), 3.41 (2H, d, J=14 Hz), 3.63 (2H, t, J=7 Hz), 7.1-7.2 (4H, m), 7.2-7.3 (6H, m);

MS m/z: 322 (M$^+$).

2-hydroxy-3-(2-naphthylmethyl)imidazo[1,2-a]pyridine (Compound 52)

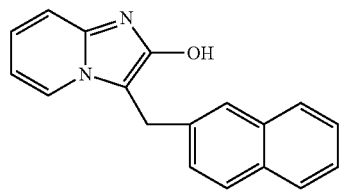 [SMILES: Oc1nc2ccccn2c1Cc1ccc2ccccc2c1]

Melting Point: 205° C. (decomposition);

NMR (CD$_3$OD-CDCl$_3$(1:1)) δ: 3.41 (1H, d, J=15 Hz), 3.76 (1H, d, J=15 Hz), 6.72 (1H, t, J=7 Hz), 7.02 (1H, d, J=9 Hz), 7.29 (1H, d, J=9 Hz), 7.4-7.5 (2H, m), 7.58 (2H, brs), 7.6-7.9 (4H, m);

MS m/z: 274 (M$^+$).

spiro[imidazo[1,2-a]pyridin-2(3H)-one-3,2'-benzo[f]indan] (Compound 53)

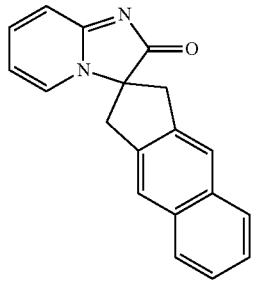 [SMILES: O=C1N=C2C=CC=CN2C12Cc1cc3ccccc3cc1C2]

Melting Point: 214° C. (decomposition);
NMR (CD$_3$OD-CDCl$_3$(1:1)) δ: 3.33 (2H, d, J=16 Hz), 4.02 (2H, d, J=16 Hz), 6.58 (1H, t, J=7 Hz), 7.16 (1H, d, J=7 Hz), 7.24 (1H, d, J=9 Hz), 7.5-7.6 (2H, m), 7.74 (1H, t, J=8 Hz), 7.8-7.9 (4H, m);
MS m/z: 286 (M$^+$).

3-benzylimidazo[1,2-a]pyridin-2(3H)-one (Compound 54)

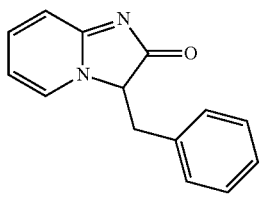 [SMILES: O=C1N=C2C=CC=CN2C1Cc1ccccc1]

Melting Point: 182° C. (decomposition);
NMR (CDCl$_3$) δ: 3.09 (1H, dd, J=8 Hz, J=15 Hz), 3.64 (1H, dd, J=4 Hz, J=15 Hz), 4.58 (1H, dd, J=4 Hz, J=8 Hz), 6.47 (1H, t, J=7 Hz), 7.0-7.1 (2H, m), 7.1-7.2 (2H, m), 7.3-7.4 (3H, m), 7.54 (1H, t, J=7 Hz);
MS m/z: 224 (M$^+$).

3,3-di(2-butenyl)imidazo[1,2-a]pyrimidin-2(3H)-one (Compound 55)

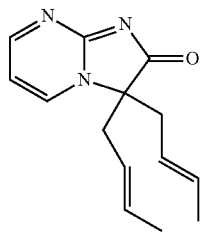 [SMILES: C/C=C/CC1(C/C=C/C)C(=O)N=C2N=CC=CN21]

Melting Point: 149.5° C. (decomposition);
NMR (CDCl$_3$) δ: 1.55 (6H, d, J=6 Hz), 2.51 (2H, dd, J=8 Hz, J=15 Hz), 2.76 (2H, dd, J=8 Hz, J=15 Hz), 5.1-5.3 (2H, m), 5.4-5.7 (2H, m), 6.69 (1H, dd, J=5 Hz, J=6 Hz), 7.75 (1H, dd, J=2 Hz, J=6 Hz), 8.7 (1H, dd, J=2 Hz, J=5 Hz);
MS m/z: 243 (M$^+$).

spiro[imidazo[1,2-a]pyridin-2(3H)-one-3,2'-(4'-fluoroindan)] (Compound 56)

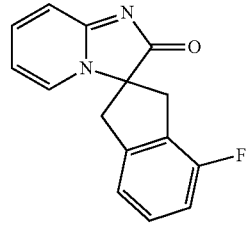 [SMILES: O=C1N=C2C=CC=CN2C12Cc1cccc(F)c1C2]

Melting Point: 148.0° C. (decomposition);
NMR (CDCl$_3$) δ: 3.24 (2H, dd, J=18 Hz, J=22 Hz), 3.88 (2H, t, J=18 Hz), 6.55 (1H, t, J=7 Hz), 7.01 (1H, t, J=9 Hz), 7.10 (1H, d, J=7 Hz), 7.2-7.3 (3H, m), 7.63 (1H, t, J=8 Hz);
MS m/z: 254 (M$^+$).

spiro[imidazo[1,2-a]pyridin-2(3H)-one-3,2'-(5'-methoxyindan)] (Compound 57)

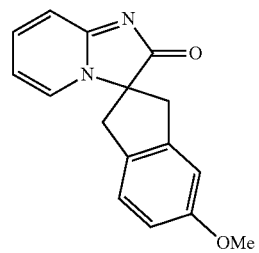 [SMILES: COc1ccc2c(c1)CC1(C2)C(=O)N=C2C=CC=CN21]

Melting Point: 150.0-152.0° C.;
NMR (CDCl$_3$) δ: 3.08 (2H, dd, J=6 Hz, J=17 Hz), 3.8-4.0 (5H, m), 6.49 (1H, t, J=7 Hz), 6.8-6.9 (2H, m), 7.1-7.3 (3H, m), 7.60 (1H, t, J=7 Hz);
MS m/z: 266 (M$^+$).

spiro[imidazo[1,2-a]pyridin-2(3H)-one-3,2'-(5'-iodoindan)] (Compound 58)

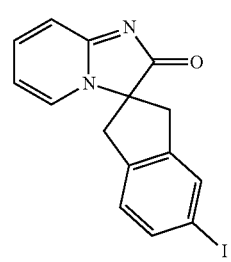 [SMILES: O=C1N=C2C=CC=CN2C12Cc1ccc(I)cc1C2]

Melting Point: 167-171° C.;
NMR (CDCl$_3$) δ: 3.14 (2H, dd, J=6 Hz, J=17 Hz), 3.82 (2H, dd, J=17 Hz, J=18 Hz), 6.57 (1H, t, J=7 Hz), 7.08 (1H, d, J=8 Hz), 7.1-7.3 (2H, m), 7.6-7.7 (3H, m);
MS m/z: 362 (M$^+$).

spiro[imidazo[1,2-a]pyridin-2(3H)-one-3,2'-(4'-cyanoindan)] (Compound 59)

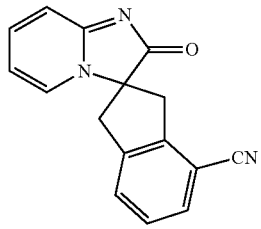 [SMILES: N#Cc1cccc2c1CC1(C2)C(=O)N=C2C=CC=CN21]

Melting Point: 247.7° C. (decomposition);

NMR (CDCl$_3$) δ: 3.26 (2H, dd, J=3 Hz, J=18 Hz), 3.93 (2H, dd, J=6 Hz, J=18 Hz), 6.56 (1H, t, J=7 Hz), 7.15 (1H, d, J=7 Hz), 7.23 (1H, d, J=9 Hz), 7.44 (1H, d, J=8 Hz), 7.6-7.7 (3H, m);

MS m/z: 261 (M$^+$).

spiro[imidazo[2,1-a]isoquinolin-2(3H)-one-3,2'-indan] (Compound 60)

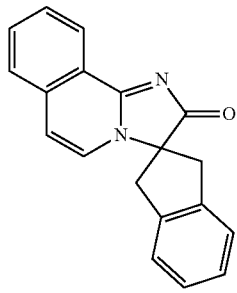 [SMILES: O=C1N=C2c3ccccc3C=CN2C12Cc1ccccc1C2]

Melting Point: 201-203° C.;

NMR (CDCl$_3$) δ: 3.22 (2H, d, J=17 Hz), 3.91 (2H, d, J=17 Hz), 6.74 (1H, d, J=7 Hz), 6.89 (1H, d, J=7 Hz), 7.32 (4H, s), 7.6-7.7 (2H, m), 7.79 (1H, t, J=7 Hz), 8.63 (1H, d, J=8 Hz);

MS m/z: 286 (M$^+$).

spiro[imidazo[1,2-a]pyridin-2(3H)-one-3,2'4(1,2,5-thiadiazo)[4,5-c]indan)] (Compound 61)

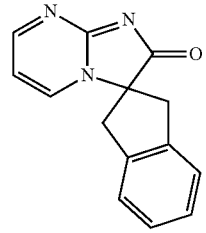

Melting Point: 86-88° C.;

NMR (CDCl$_3$-CD$_3$OD(1:1)) δ: 3.44 (2H, d, J=18 Hz), 4.00 (2H, d, J=18 Hz), 6.71 (1H, t, J=7 Hz), 7.2-7.4 (2H, m), 7.81 (1H, t, J=7 Hz), 7.97 (2H, s);

MS m/z: 294 (M$^+$).

spiro[imidazo[2,1-a]isoquinolin-2(3H)-one-3,2'-((1,2,5-thiadiazo)[4,5-c]indan)] (Compound 62)

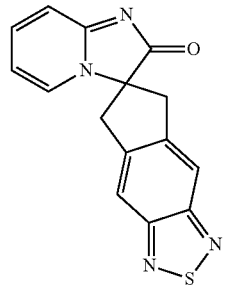 [SMILES: O=C1N=C2C=CC=CN2C12Cc1cc3nsnc3cc1C2]

Melting Point: 271.5° C. (decomposition);

NMR (CDCl$_3$) δ: 3.39 (2H, d, J=16 Hz), 4.04 (2H, brd, J=16 Hz), 6.77 (1H, d, J=7 Hz), 6.81 (1H, d, J=7 Hz), 7.6-7.8 (2H, m), 7.82 (1H, brs, J=8 Hz), 7.95 (2H, brs), 8.65 (1H, d, J=8 Hz);

MS m/z: 344 (M$^+$).

spiro[imidazo[1,2-a]pyrimidin-2(3H)-one-3,2'-indan] (Compound 63)

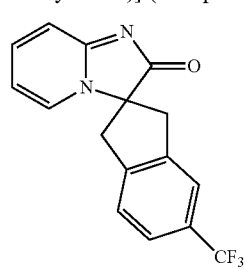

Melting Point: 195.5° C. (decomposition);

NMR (CDCl$_3$) δ: 3.17 (2H, d, J=17 Hz), 3.92 (2H, d, J=17 Hz), 6.53 (1H, dd, J=5 Hz, J=6 Hz), 7.44 (1H, dd, J=2 Hz, J=6 Hz), 7.32 (4H, s), 8.72 (1H, dd, J=2 Hz, J=5 Hz);

MS m/z: 237 (M$^+$).

spiro[imidazo[1,2-a]pyridin-2(3H)-one-3,2'-(5'-trifluoromethylindan)] (Compound 64)

Melting Point: 176.5-179.5° C.;

NMR (CDCl$_3$) δ: 3.25 (2H, d, J=17 Hz), 3.92 (2H, d, J=17 Hz), 6.57 (1H, t, J=7 Hz), 7.1-7.2 m), 7.44 (1H, d, J=8 Hz), 8.5-8.7 (3H, m);

MS m/z: 304 (M$^+$).

spiro[imidazo[1,2-a]pyridin-2(3H)-one-3,2'-benzo[e]indan] (Compound 65)

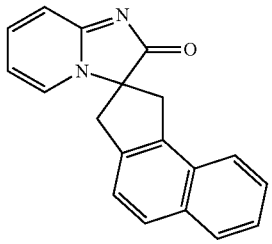 [SMILES: O=C1N=C2C=CC=CN2C12Cc1ccc3ccccc3c1C2]

Melting Point: 256.0° C. (decomposition);
NMR (CDCl$_3$) δ: 3.33 (1H, d, J=17 Hz), 3.56 (1H, d, J=17 Hz), 4.09 (2H, t, J=17 Hz), 6.50 (1H, t, J=7 Hz), 7.22 (1H, d, J=9 Hz), 7.29 (1H, d, J=7 Hz), 7.42 (1H, d, J=8 Hz), 7.5-7.7 (4H, m), 7.83 (1H, d, J=8 Hz), 7.92 (1H, d, J=6 Hz);
MS m/z: 286 (M$^+$).

3,3-diallylimidazo[1,2-a]pyridin-2(3H)-one (Compound 66)

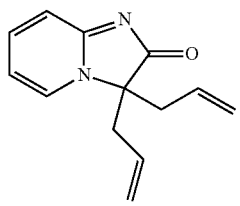 [SMILES: C=CCC1(CC=C)C(=O)N=C2C=CC=CN21]

Melting Point: 64-66° C.;
NMR (CDCl$_3$) δ: 2.56 (2H, dd, J=9 Hz, J=14 Hz), 2.86 (2H, dd, J=6 Hz, J=14 Hz), 4.99 (2H, dd, J=1 Hz, J=7 Hz), 5.40 (2H, d, J=1 Hz), 5.4-5.6 (2H, m), 6.67 (1H, t, J=7 Hz), 7.17 (1H, d, J=7 Hz), 7.52 (1H, d, J=7 Hz), 7.59 (1H, d, J=7 Hz);
MS m/z: 214 (M$^+$).

3,3-bis(2-cyclohexenyl)imidazo[1,2-a]pyridin-2(3H)-one (Compound 67)

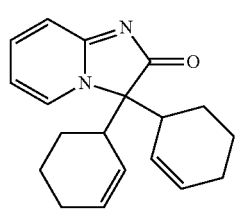 [SMILES: O=C1N=C2C=CC=CN2C1(C1C=CCCC1)C1C=CCCC1]

Melting Point: 245-247° C.;
NMR (CDCl$_3$) δ: 1.4-2.0 (12H, m), 2.9-3.1 (2H, m), 5.29 (1H, brd, J=10 Hz), 5.8-6.0 (3H, m), 6.62 (1H, t, J=7 Hz), 7.17 (1H, d, J=9 Hz), 7.5-7.7 (2H, m);
MS m/z: 294 (M$^+$).

3,3-diallylimidazo[2,1-a]isoquinolin-2(3H)-one (Compound 68)

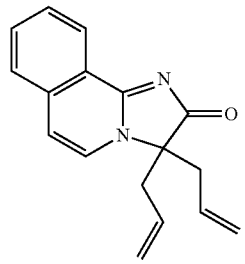 [SMILES: C=CCC1(CC=C)C(=O)N=C2c3ccccc3C=CN21]

Melting Point: 108-110° C.;
NMR (CDCl$_3$) δ: 2.62 (2H, dd, J=8 Hz, J=14 Hz), 2.89 (2H, dd, J=6 Hz, J=14 Hz), 4.9-5.1 (4H, m), 5.4-5.6 (2H, m), 6.91 (1H, d, J=7 Hz), 7.25 (1H, d, J=7 Hz), 7.6-7.7 (2H, m), 7.80 (1H, t, J=8 Hz), 8.57 (1H, d, J=8 Hz);
MS m/z: 264 (M$^+$).

Exemplary Preparation 5

An exemplary preparation of spiro[imidazo[2,1-a]isoquinolin-2(3H)-one-3,4'-(1'-cyclopentene)] (Compound 69) having the general formula below is described hereafter.

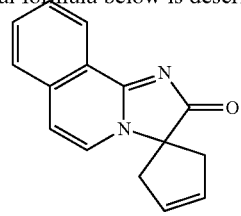

An amount of 80 mg of Grubbs reagent (0.24 mmol) was added to a chloroform solution (80 ml) of 1.0 g (3.8 mmol) of 3,3-diallylimidazo[2,1-a]isoquinolin-2(3H)-one obtained in the same manner as in Exemplary Preparation 1 under an argon atmosphere and heated under flux for 14 hours. The reaction mixture was allowed to stand for cooling and the solvent was removed by distillation under reduced pressure. Water was added to the residue and the mixture was extracted with dichloromethane several times. The extracted layers were rinsed together with saturated brine and dried over anhydrous magnesium sulfate. The solvent was removed by distillation under reduced pressure and the residue was chromatographed over silica gel column for purification (ethyl acetate:methanol=10:1) to obtain 748 mg (83.5%) of the title compound in the form of light brown crystals.

Results of analysis of the obtained compound are given below. The results show that the obtained compound was the targeted compound.

Melting Point: 173.5° C. (decomposition);
NMR (CDCl$_3$) δ: 2.70 (2H, d, J=17 Hz), 3.30 (2H, d, J=17 Hz), 5.92 (2H, s), 6.89 (1H, d, J=7 Hz), 7.33 (1H, d, J=7 Hz), 7.6-7.8 (2H, m), 7.79 (1H, t, J=7 Hz), 8.60 (1H, d, J=7 Hz);
MS m/z: 236 (M$^+$).

Exemplary Preparation 6

Compound 70 having the general formula below corresponding to starting materials was prepared in the same manner as in Exemplary Preparation 5. Results of analysis of the obtained compound are given below for each compound. The results show that the obtained compound was the targeted Compound 70.

spiro[8-benzyloxyimidazo[1,2-a]pyridin-2(3H)-one-3,4'-(1'-cyclopentene)] (Compound 70)

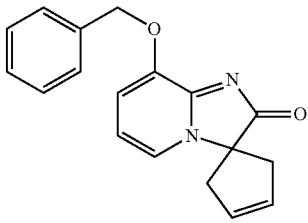 [SMILES: O=C1N=C2C(OCc3ccccc3)=CC=CN2C12CC=CC2]

Melting Point: 178.5-180.5° C.;

NMR (CDCl$_3$) δ: 2.64 (2H, d, J=16 Hz), 3.29 (2H, d, J=16 Hz), 5.30 (2H, s), 5.88 (2H, s), 6.49 (1H, dd, J=6 Hz, J=8 Hz), 6.94 (1H, dd, J=6 Hz, J=8 Hz), 6.94 (1H, d, J=8 Hz), 7.2-7.5 (5H, m);

MS m/z: 292 (M$^+$).

Exemplary Preparation 7

An exemplary preparation of 3,3-dipropyl-5,6,7,8-tetrahydroimidazo[1,2-a]pyridin-2(3H)-one (Compound 71) having the general formula below is described hereafter.

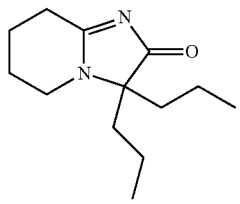

An amount of 100 mg of 10% palladium on carbon was added to an ethanol solution (30 ml) of 300 mg (1.4 mmol) of 3,3-diallylimidazo[1,2-a]pyridin-2(3H)-one obtained in the same manner as in Exemplary Preparation 5 and the mixture was subject to catalytic reduction at room temperature under a hydrogen atmosphere overnight. The insoluble substances were filtered off and the solvent was removed from the filtrate by distillation under reduced pressure. The residue was chromatographed over silica gel column (hexane:ethyl acetate=10:1) to obtain 281 mg (90.3%) of the title compound in the form of crystals. Recrystallization from hexane-ethyl acetate (10:1) yielded white crystals having a melting point of 98.5-101° C.

Results of analysis of the obtained compound are given below. The results show that the obtained compound was the targeted compound.

NMR (CDCl$_3$) δ: 0.86 (6H, t, J=7 Hz), 0.9-1.1 (2H, m), 1.1-1.2 (2H, m), 1.4-1.6 (2H, m), 1.7-2.0 (6H, m), 2.79 (2H, t, J=6 Hz), 3.19 (2H, t, J=6 Hz);

MS m/z: 222 (M$^+$).

Exemplary Preparation 8

Compounds 72 to 77 having the general formulae corresponding to starting materials were prepared in the same manner as in Exemplary Preparation 7.

Results of analysis of the obtained compounds are given below for each compound. The results show that the obtained compounds were the targeted Compounds 72 to 3,3-dicyclohexyl-5,6,7,8-tetrahydroimidazo[1,2-a]pyridin-2(3H)-one (Compound 72)

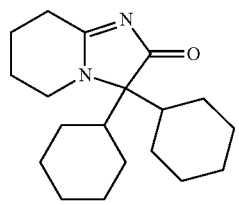 [SMILES: O=C1N=C2CCCCN2C1(C1CCCCC1)C1CCCCC1]

Melting Point: 218-220° C.;

NMR (CDCl$_3$) δ: 0.9-1.4 (8H, m), 1.5-2.0 (18H, m), 2.79 (2H, t, J=6 Hz), 3.30 (2H, t, J=6 Hz);

MS m/z: 302 (M$^+$).

3,3-dibutyl-5,6,7,8-tetrahydroimidazo[1,2-a]pyridin-2(3H)-one (Compound 73)

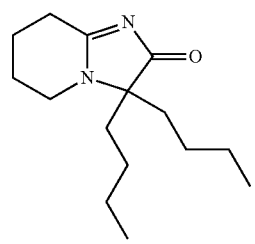 [SMILES: CCCCC1(CCCC)C(=O)N=C2CCCCN21]

Melting Point: 35-40° C.;

NMR (CDCl$_3$) δ: 0.88 (6H, t, J=7 Hz), 0.9-1.4 (8H, m), 1.6-2.2 (8H, m), 3.2-3.4 (4H, m);

MS m/z: 250 (M$^+$).

spiro[7,8,9,10-tetrahydroimidazo[2,1-a]isoquinolin-2(3H)-one-3,1'-cyclopentane] (Compound 74)

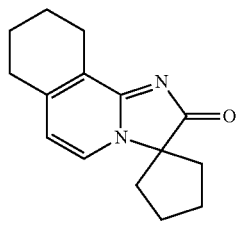 [SMILES: O=C1N=C2C3=C(C=CN2C12CCCC2)CCCC3]

Melting Point: 270.5° C. (decomposition);

NMR (CDCl$_3$) δ: 1.8-2.2 (10H, m), 2.3-2.5 (2H, m), 2.6-2.8 (4H, m), 6.44 (1H, d, J=7 Hz), 7.35 (1H, d, J=7 Hz);

MS m/z: 242 (M$^+$).

spiro[imidazo[2,1-a]isoquinolin-2(3H)-one-3,1'-cyclopentane] (Compound 75)

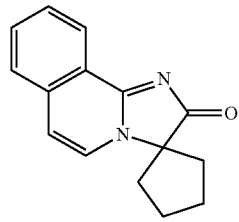 [SMILES: O=C1N=C2c3ccccc3C=CN2C12CCCC2]

Melting Point: 164.5-167.5° C.;
NMR (CDCl$_3$) δ: 1.8-2.3 (6H, m), 2.4-2.6 (2H, m), 6.94 (1H, d, J=7 Hz), 7.33 (1H, d, J=7 Hz), 7.6-7.7 (2H, m), 7.79 (1H, t, J=6 Hz), 8.60 (1H, d, J=8 Hz);
MS m/z: 238 (M$^+$).

spiro[5,6,7,8-tetrahydroimidazo[1,2-a]pyridin-2(3H)-one-3,2'-benzo[f]indan] (Compound 76)

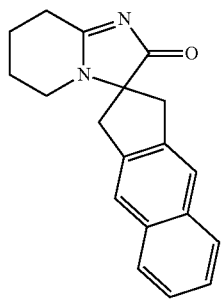 [SMILES: O=C1N=C2CCCCN2C12Cc1cc3ccccc3cc1C2]

Melting Point: 252.5° C. (decomposition);
NMR (CDCl$_3$-CD$_3$OD(1:1)) δ: 1.9-2.1 (4H, m), 3.0-3.2 (4H, m), 3.50 (2H, d, J=18 Hz), 3.79 (2H, d, J=18 Hz), 7.4-7.5 (2H, m), 7.75 (2H, s), 7.8-7.9 (2H, m);
MS m/z: 290 (M$^+$).

spiro[5,6,7,8-tetrahydroimidazo[1,2-a]pyridin-2(3H)-one-3,2'-indan] (Compound 77)

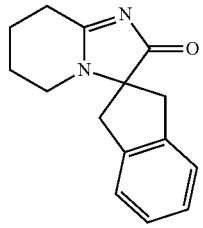 [SMILES: O=C1N=C2CCCCN2C12Cc1ccccc1C2]

Melting Point: 276.5° C. (decomposition);
NMR (CDCl$_3$-CD$_3$OD (1:1)) δ: 1.9-2.1 (4H, m), 3.0-3.3 (4H, m), 3.45 (2H, d, J=17 Hz), 3.66 (2H, d, J=17 Hz), 7.30 (4H, s);
MS m/z: 240 (M$^+$).

Exemplary Preparation 9

Compounds 78 to 81 having the general formulae corresponding to starting materials were each prepared in the same manner as in Exemplary Preparation 1. Results of analysis of the obtained compounds are given below for each compound. The results show that the obtained compounds were the targeted Compounds 78 to 81.

3,3-bis(4-chlorobenzyl)imidazo[1,2-a]pyridin-2(3H)-one (Compound 78)

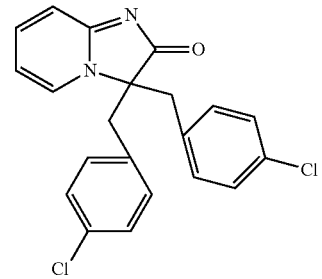 [SMILES: O=C1N=C2C=CC=CN2C1(Cc1ccc(Cl)cc1)Cc1ccc(Cl)cc1]

Melting Point: 293.0-296.0 (° C.).
$^1$H-NMR (CDCl$_3$) δ: 3.11 (2H, d, J=14 Hz), 3.55 (2H, d, J=14 Hz), 6.62 (1H, t, J=7 Hz), 6.78 (1H, d, J=8 Hz), 6.94 (4H, d, J=8 Hz), 7.12 (4H, d, J=8 Hz), 7.40 (1H, t, J=7 Hz), 7.47 (1H, d, J=7 Hz);
MS m/z: 382 (M+)

8-cyclopropylmethyloxy-3,3-diallylimidazo[1,2-a]pyridin-2(3H)-one (Compound 79)

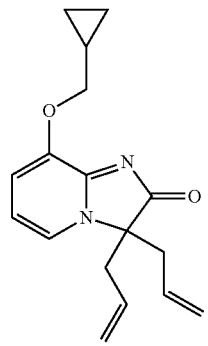 [SMILES: C=CCC1(CC=C)C(=O)N=C2C(OCC3CC3)=CC=CN21]

Melting Point: 139.0-142.0 (° C.);
$^1$H-NMR (CDCl$_3$) δ: 0.35-0.40 (2H, m), 0.60-0.65 (2H, m), 1.30-1.40 (1H, m), 2.50-2.60 (2H, m), 2.80-2.90 (2H, m), 3.94 (2H, d, J=7 Hz), 4.96 (2H, brs), 5.02 (2H, brs), 5.40-5.65 (2H, m), 6.57 (1H, t, J=7 Hz, J=8 Hz), 6.91 (1H, d, J=8 Hz), 7.16 (1H, d, J=7 Hz);
MS m/z: 284 (M$^+$).

spiro[imidazo[1,2-a]pyridin-2(3H)-one-3,2'-(4'-hydroxy-indan)] (Compound 80)

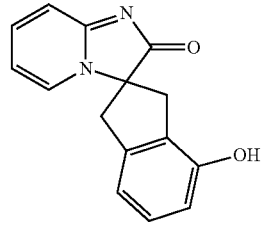 [SMILES: O=C1N=C2C=CC=CN2C12Cc1cccc(O)c1C2]

Melting Point: 240.0° C. (dec.);
$^1$H-NMR (CD$_3$OD) δ: 3.17 (1H, d, J=17 Hz), 3.19 (1H, d, J=17 Hz), 3.50 (1H, d, J=17 Hz), 3.61 (1H, d, J=17 Hz), 6.63 (1H, d, J=8 Hz), 6.70-6.80 (2H, m), 7.07 (1H, d, J=8 Hz), 7.12 (1H, d, J=9 Hz), 7.51 (1H, d, J=7 Hz), 7.81 (1H, d, J=8 Hz);
MS m/z: 352 (M$^+$).

spiro[8-hydroxy-imidazo[1,2-a]pyridin-2(3H)-one-3,2'-indan] (Compound 81)

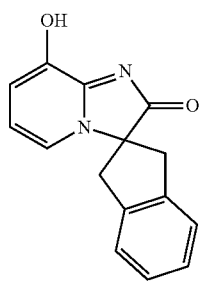 [SMILES: O=C1N=C2C(O)=CC=CN2C12Cc1ccccc1C2]

Melting Point: 285.0-290.0° C.;
$^1$H-NMR (CDCl$_3$) δ: 3.22 (2H, d, J=17 Hz), 3.91 (2H, d, J=17 Hz), 6.57 (1H, dd, J=6 Hz, J=7 Hz), 6.82 (1H, d, J=6 Hz), 7.27 (1H, d, J=7 Hz), 7.31 (4H, s);
MS m/z: 352 (M$^+$).

Exemplary Preparation 10

Compounds 82 to 83 having the general formulae corresponding to starting materials were each prepared in the same manner as in Exemplary Preparation 5. Results of analysis of the obtained compounds are given below for each compound. The results show that the obtained compounds were the targeted Compounds 82 to 83.

spiro[8-methoxyimidazo[1,2-a]pyridin-2(3,4')-one-3,4'-(1'-cyclopentene)] (Compound 82)

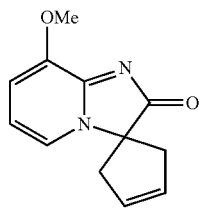 [SMILES: COC1=CC=CN2C1=NC(=O)C21CC=CC1]

Melting Point: 200.0-202.0° C.;
$^1$H-NMR (CDCl$_3$): 2.64 (2H, d, J=17 Hz), 3.29 (2H, d, J=17 Hz), 3.96 (3H, s), 5.88 (2H, s), 6.57 (1H, dd, J=7 Hz, J=8 Hz), 6.91 (1H, d, J=8 Hz), 7.29 (1H, d, J=7 Hz);
MS m/z: 216 (M$^+$).

spiro[8-cyclopropylmethyloxyimidazo[1,2-a]pyridin-2(3H)-one-3,4'-(1'-cyclopentene)] (Compound 83)

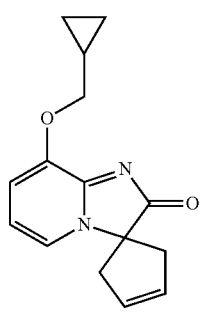 [SMILES: O=C1N=C2C(OCC3CC3)=CC=CN2C12CC=CC2]

Melting Point: 134.0-137.0° C.;
$^1$H-NMR (CDCl$_3$) δ: 0.35-0.40 (2H, m), 0.60-0.70 (2H, m), 1.30-1.40 (1H, m), 2.64 (2H, d, J=16 Hz), 3.28 (2H, d, J=16 Hz), 3.98 (2H, d, J=7 Hz), 5.88 (2H, s), 6.54 (1H, dd, J=7 Hz, J=8 Hz), 6.92 (1H, d, T=8 Hz), 7.28 (1H, d, J=7 Hz);
MS m/z: 256 (M$^+$).

Exemplary Pharmaceutical Formulation.

The following table shows a typical pharmaceutical composition that may be administered according to the invention.

| Component | Quantity per 10 mg tablet | Quantity per 60 mg tablet |
|---|---|---|
| Compound 24 | 10 mg | 60 mg |
| Mannitol | 95.9 mg | 45.9 mg |
| Microcrystalline cellulose | 19.3 mg | 19.3 mg |
| Low-substituted hydroxypropyl cellulose | 7.0 mg | 7.0 mg |
| Hydroxypropyl cellulose | 5.0 mg | 5.0 mg |
| Magnesium stearate | 2.8 mg | 2.8 mg |
| Total | 140.0 mg | 140.0 mg |

The present invention is described above using examples. The examples are given by way of example. It is understood by a person in the art that various modifications are available and those modifications are included in the scope of the present invention.

For example, the above examples used mice as a mammal. However, other mammals including human can be used. Even in such cases, the above Compounds 1 to 83 exhibit antidepressant, neuroprotection, amyloid β deposition inhibitory, or age retardant activity in other mammals including human.

What is claimed is:

1. A method of treating hair loss in an animal in need thereof, comprising administering to the animal an effective amount of spiro[imidazo[1,2-a]pyridin-2(3H)-one-3,2'-indan] or a pharmaceutically acceptable salt or hydrate thereof.

2. The method according to claim 1, wherein said administration is oral.

* * * * *